United States Patent
Lebl et al.

(10) Patent No.: US 7,390,459 B2
(45) Date of Patent: *Jun. 24, 2008

(54) OLIGONUCLEOTIDE SYNTHESIZER

(75) Inventors: Michal Lebl, San Diego, CA (US); David L. Heiner, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 125 days.

This patent is subject to a terminal disclaimer.

(21) Appl. No.: 09/881,052

(22) Filed: Jun. 13, 2001

(65) Prior Publication Data

US 2002/0044894 A1   Apr. 18, 2002

Related U.S. Application Data

(63) Continuation-in-part of application No. 09/738,473, filed on Dec. 13, 2000, now Pat. No. 6,663,832.

(60) Provisional application No. 60/170,314, filed on Dec. 13, 1999.

(51) Int. Cl.
*G01N 33/48* (2006.01)
(52) U.S. Cl. .......................... 422/64; 436/45
(58) Field of Classification Search ................ 422/64, 422/100, 67; 436/45, 180; 73/863.01, 863.44, 73/867.31
See application file for complete search history.

(56) References Cited

U.S. PATENT DOCUMENTS

| | | | |
|---|---|---|---|
| 3,219,416 A | * | 11/1965 | Natelson ...................... 422/64 |
| 3,586,484 A | | 6/1971 | Anderson |
| 3,712,535 A | | 1/1973 | Genese et al. |

(Continued)

FOREIGN PATENT DOCUMENTS

EP   0445915 A1   9/1991

(Continued)

OTHER PUBLICATIONS

"Spyder Technology: A New Approach to Automated Solid Phase Synthesis Based on Centrifugation of Tilted Plates."*

(Continued)

*Primary Examiner*—Jill Warden
*Assistant Examiner*—Natalia Levkovich
(74) *Attorney, Agent, or Firm*—Knobbe, Martens, Olson & Bear LLP

(57) ABSTRACT

An apparatus for high-throughput combinatorial syntheses of organic molecules including a reaction vessel for containing a combinatorial-chemistry synthetic reaction, a liquid dispenser for dispensing the liquid, a liquid aspirator and an adjustment mechanism. The reaction vessel includes an ingress aperture allowing a liquid to enter into an interior of the vessel and an egress aperture for aspirating the liquid from the vessel. The liquid dispenser dispenses liquid through the ingress aperture. The liquid aspirator aspirates liquid through the egress aperture and includes a rotor for carrying the vessel and orbiting the vessel about an axis of rotation. The rotor is oriented generally in a horizontal plane and includes an adjustment mechanism for adjusting the angle of the vessel relative to the horizontal plane in response to the centrifugal force generated by orbiting the vessel about the axis of rotation. A method of combinatorial synthesis of organic molecules is also disclosed.

15 Claims, 12 Drawing Sheets

U.S. PATENT DOCUMENTS

| | | | |
|---|---|---|---|
| 3,901,656 A * | 8/1975 | Durkos et al. | 436/47 |
| 4,042,338 A * | 8/1977 | Huber | 422/64 |
| 4,244,694 A | 1/1981 | Farina et al. | |
| 4,287,154 A | 9/1981 | Sommers | |
| 4,412,973 A | 11/1983 | Guigan | |
| 4,808,380 A * | 2/1989 | Minekane | 422/64 |
| 4,837,159 A * | 6/1989 | Yamada | 436/45 |
| 4,844,868 A * | 7/1989 | Rokugawa | 422/64 |
| 4,862,932 A | 9/1989 | Feinstein et al. | |
| 4,906,433 A | 3/1990 | Minekane | |
| 5,084,242 A | 1/1992 | Sakuma et al. | |
| 5,089,417 A | 2/1992 | Wogoman | |
| 5,202,418 A | 4/1993 | Lebl et al. | |
| 5,338,831 A | 8/1994 | Lebl et al. | |
| 5,342,585 A | 8/1994 | Lebl et al. | |
| 5,434,083 A | 7/1995 | Mitsumaki et al. | |
| 5,472,672 A * | 12/1995 | Brennan | 422/131 |
| 5,501,984 A | 3/1996 | Hofstetter et al. | |
| 5,585,068 A | 12/1996 | Panetz et al. | |
| 5,660,988 A | 8/1997 | Duck et al. | |
| 5,705,062 A | 1/1998 | Knobel | |
| 6,045,755 A | 4/2000 | Lebl et al. | |
| 6,121,054 A * | 9/2000 | Lebl | 436/177 |
| 6,357,907 B1 | 3/2002 | Cleveland et al. | |
| 6,365,412 B1 * | 4/2002 | Feygin | 436/45 |
| 6,375,898 B1 | 4/2002 | Ulrich | |
| 6,423,536 B1 * | 7/2002 | Jovanovich et al. | 435/287.2 |
| 6,663,832 B2 * | 12/2003 | Lebl et al. | 422/64 |

FOREIGN PATENT DOCUMENTS

| | | |
|---|---|---|
| EP | 0569115 A3 | 11/1992 |
| FR | 2156519 | 6/1973 |
| GB | 1241539 | 8/1971 |
| JP | 59119268 A * | 7/1984 |
| JP | 61-139756 | 6/1986 |
| WO | WO 90/05590 | 5/1990 |
| WO | WO 93/10455 | 5/1993 |
| WO | WO 99/09394 A1 | 2/1999 |
| WO | WO 99/25470 | 5/1999 |
| WO | WO 99/34931 A1 | 7/1999 |
| WO | WO 00/44491 A3 | 8/2000 |

OTHER PUBLICATIONS

Lebl, M. "New Technique for High-Throughput Synthesis," Bioorganic & Medicinal Chemistry Letters, 9:1305-1310 (1999).

Lebl, M., "A new Approach to Automated Solid Phase Synthesis Based on Centrifugation of Tilted Plates," Journal of the Association for Laboratory Automation, 3(3): 59-61 (1998).

Menotti et al., "Facile Manual Synthesis of Peptide Libraries," Protein and Peptide Letters, 1(3): 187-192 (1994).

Foust et al., "Principles of Unit Operations," John Wiley & Sons, New York, 628 (1980).

Birr, C, Aspects of the Merrifield Peptide Synthesis, Springer-Verlag, New York, entire book, 101 pages (1978).

* cited by examiner

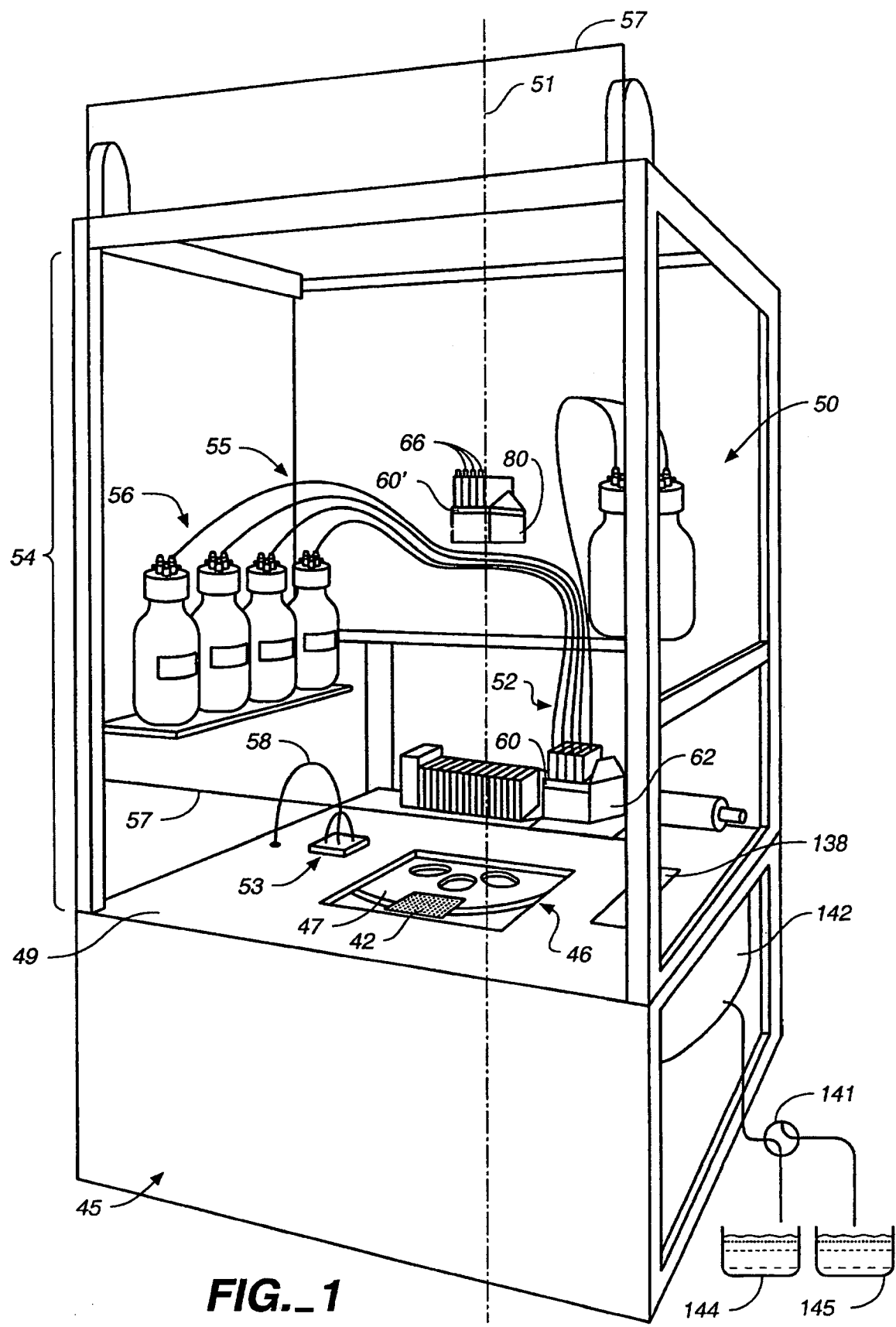
FIG._1

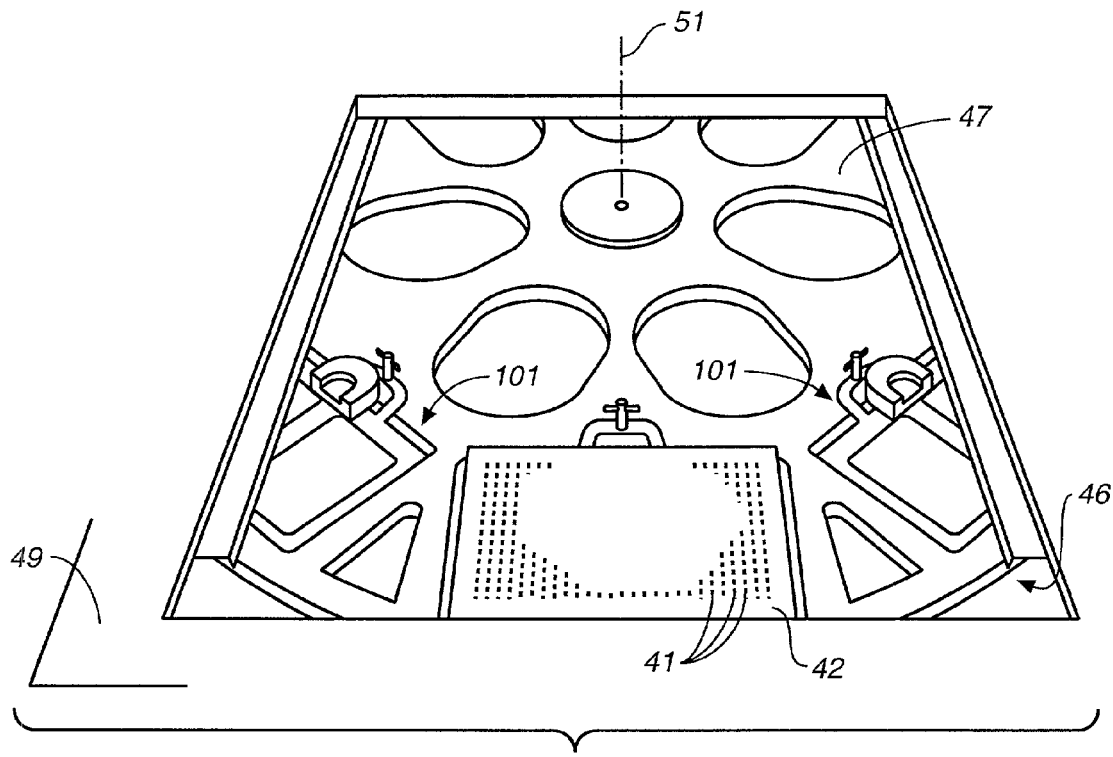
FIG._2
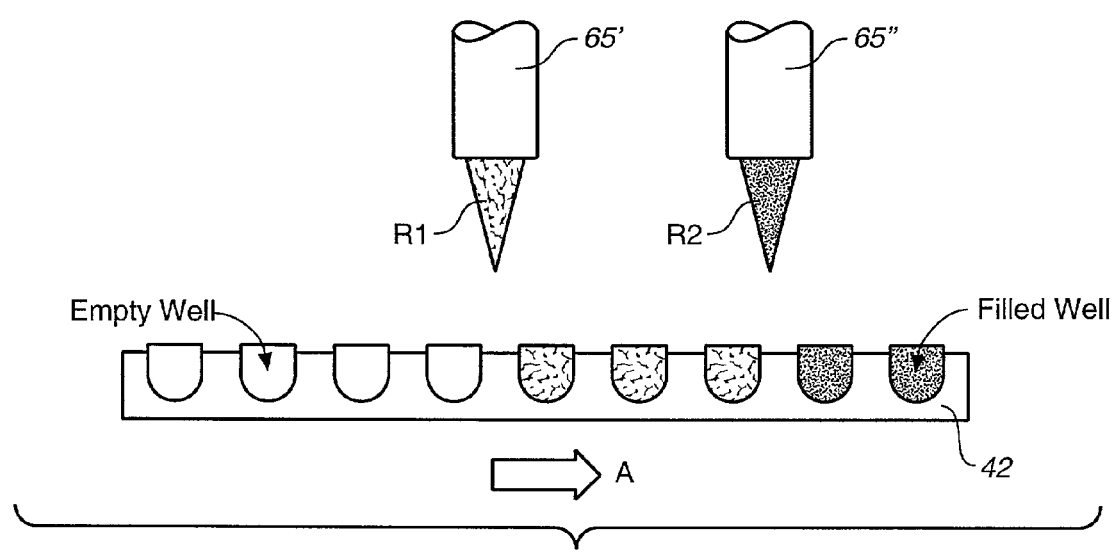
FIG._3

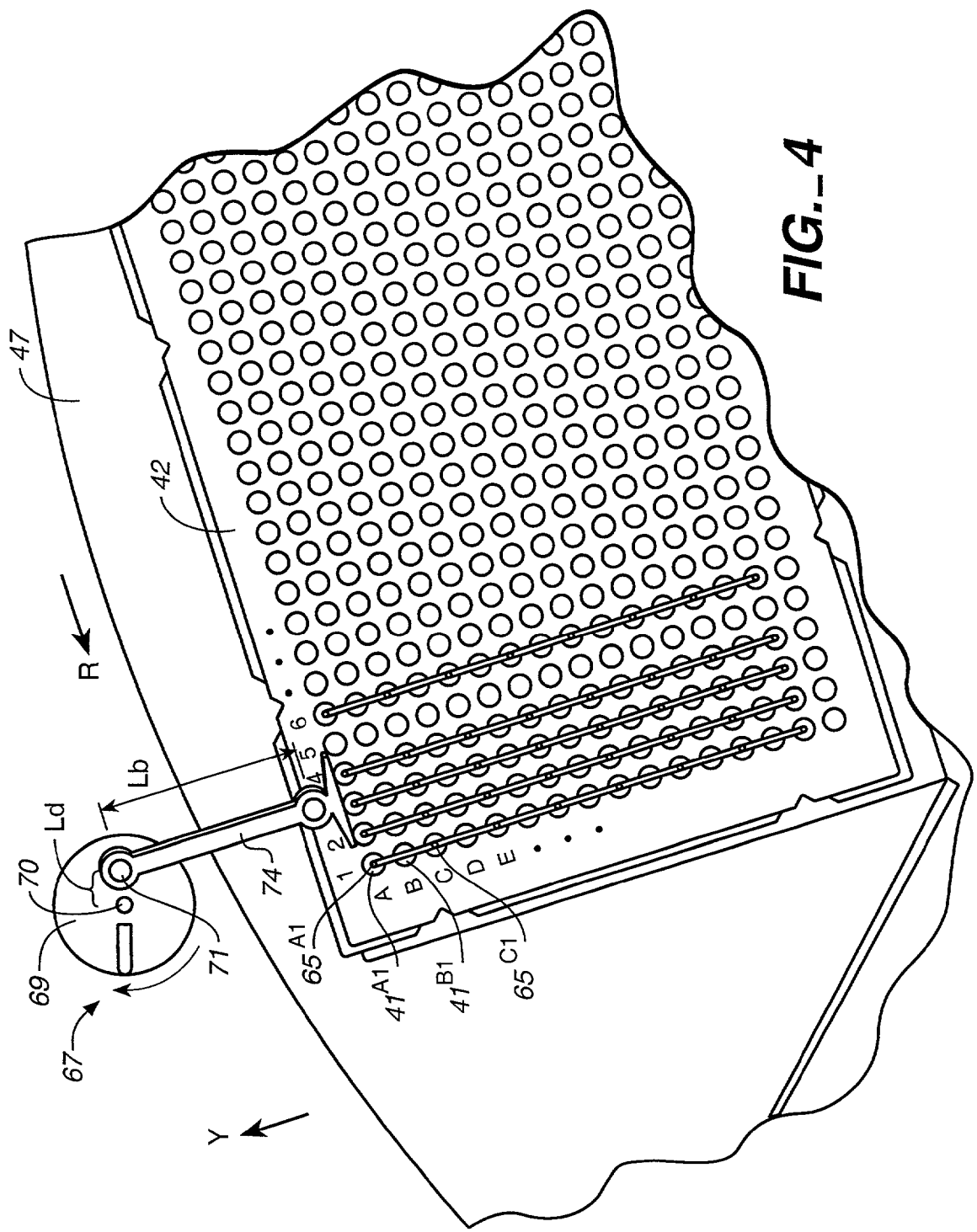
FIG._4

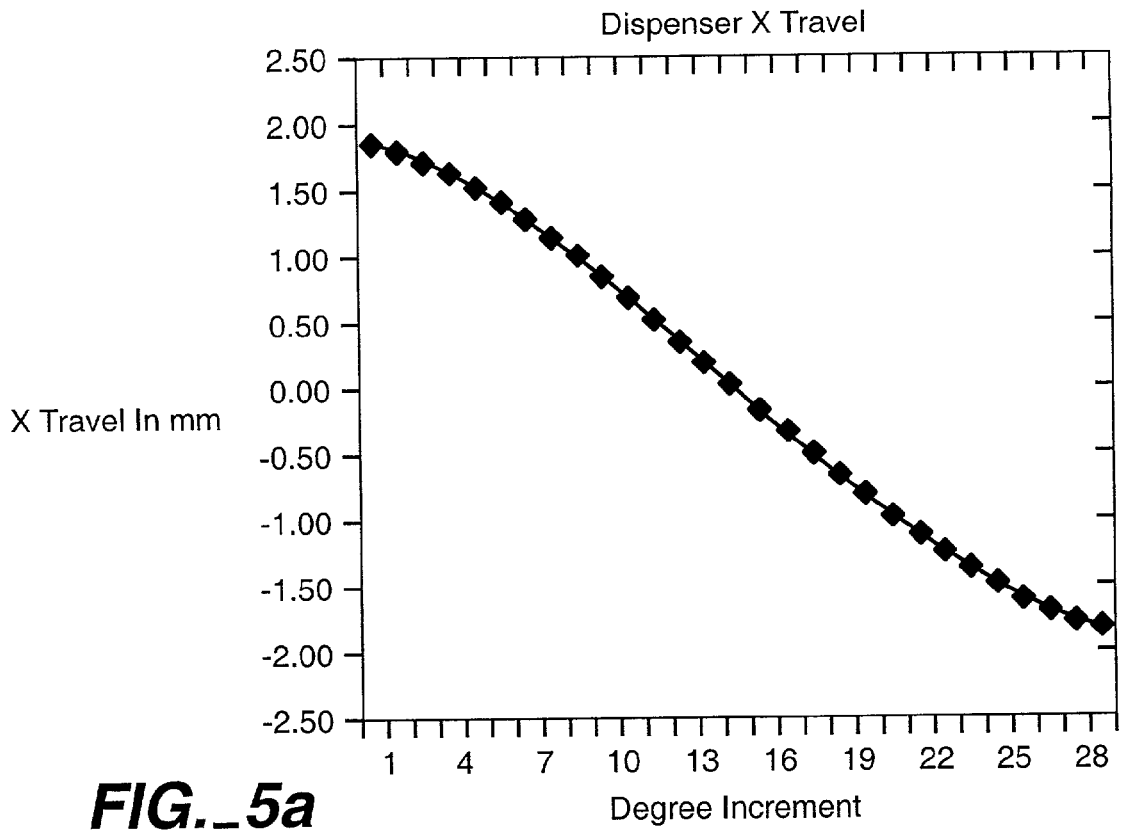
FIG._5a
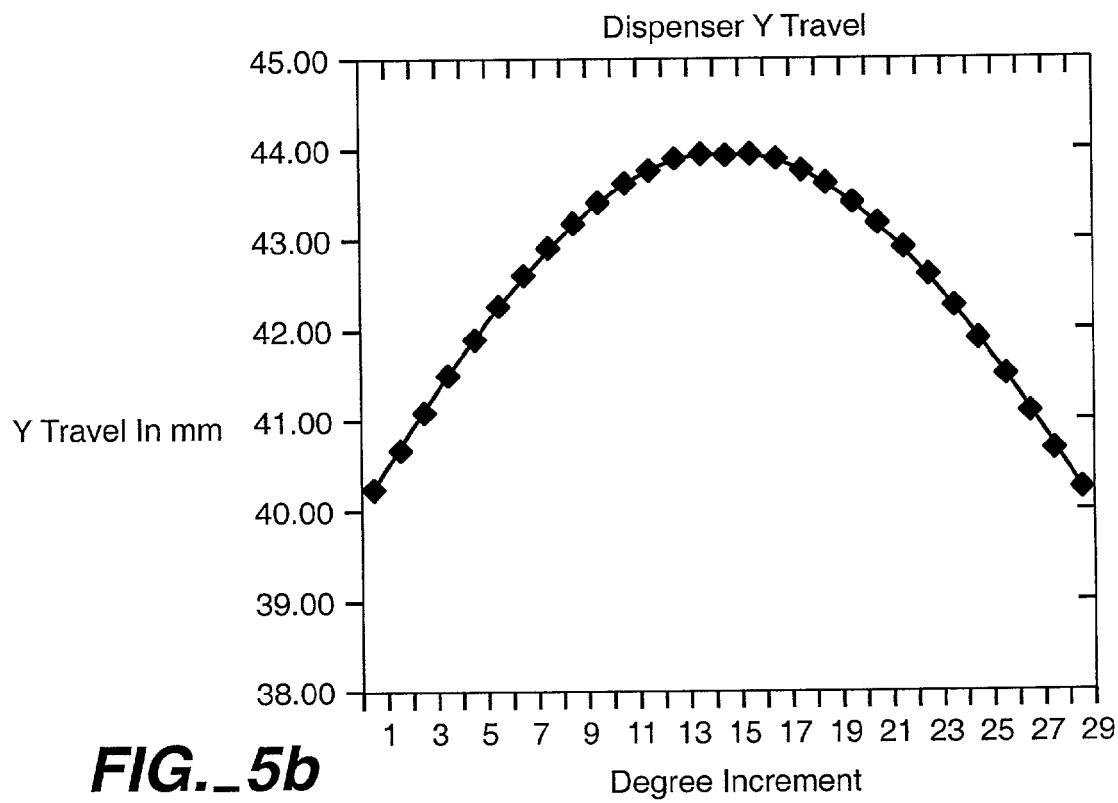
FIG._5b

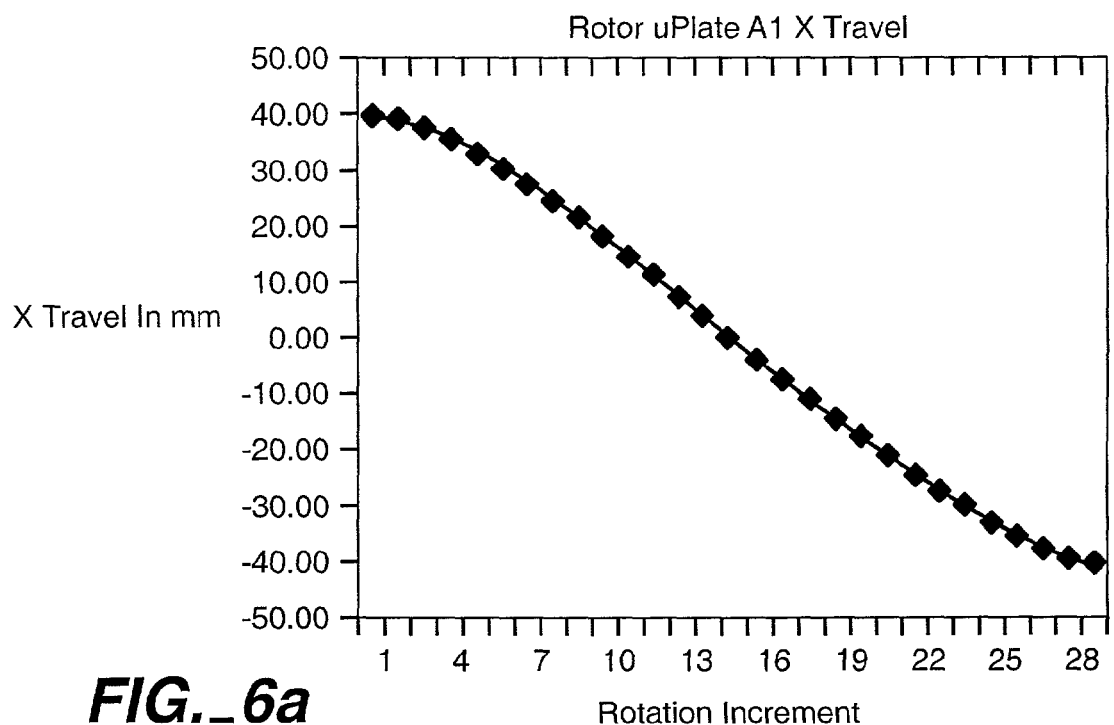
FIG._6a
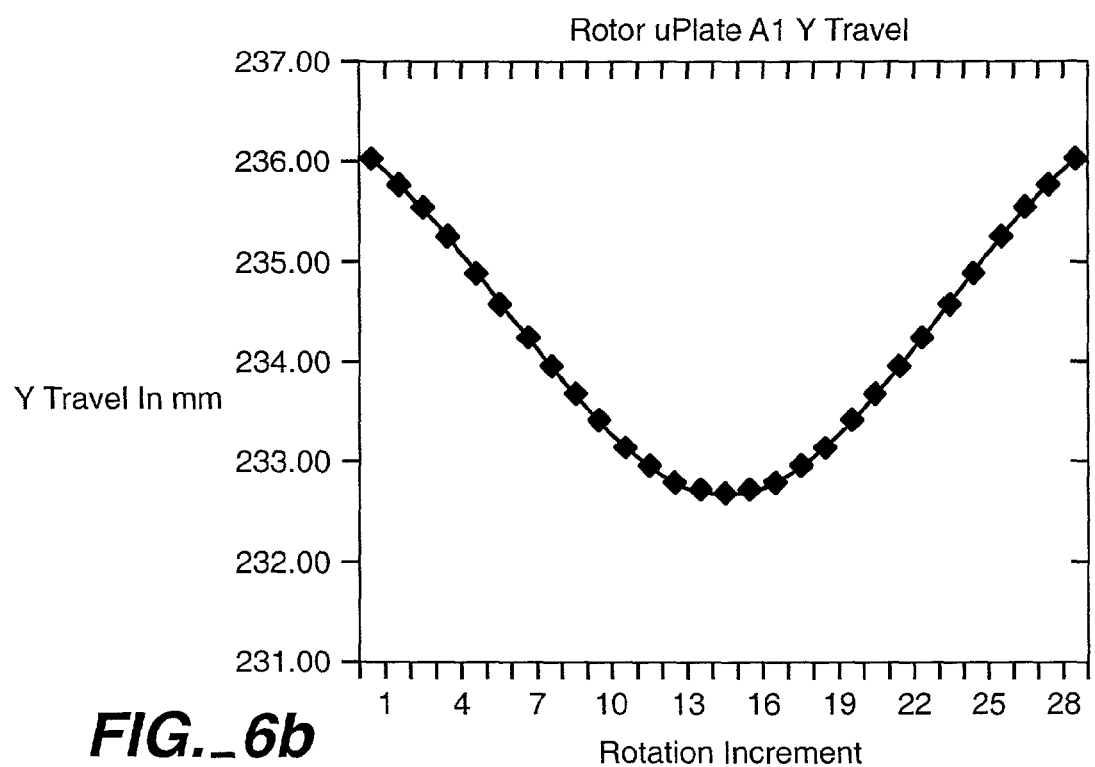
FIG._6b

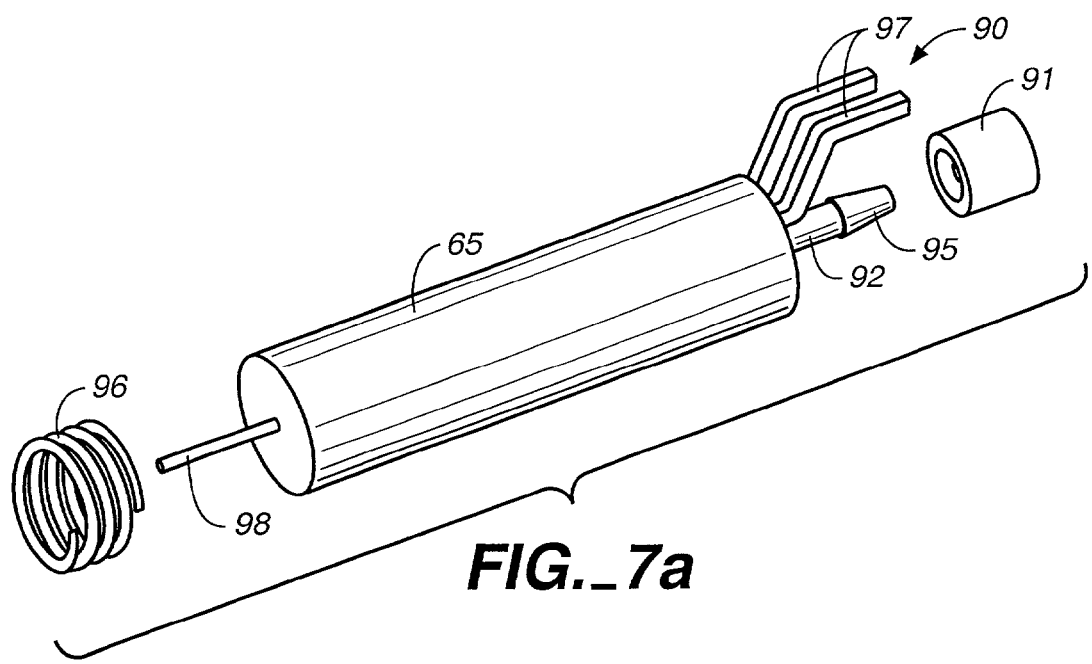
FIG._7a
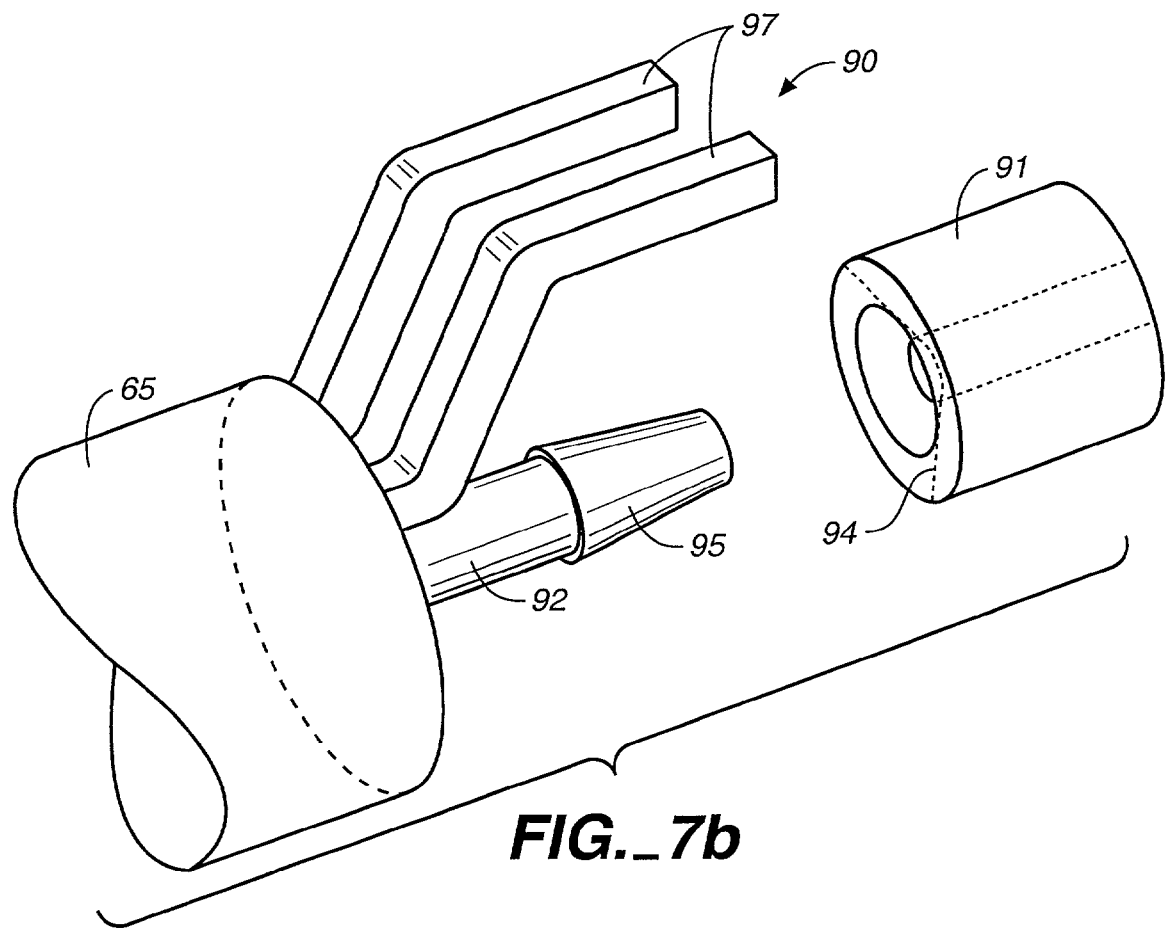
FIG._7b

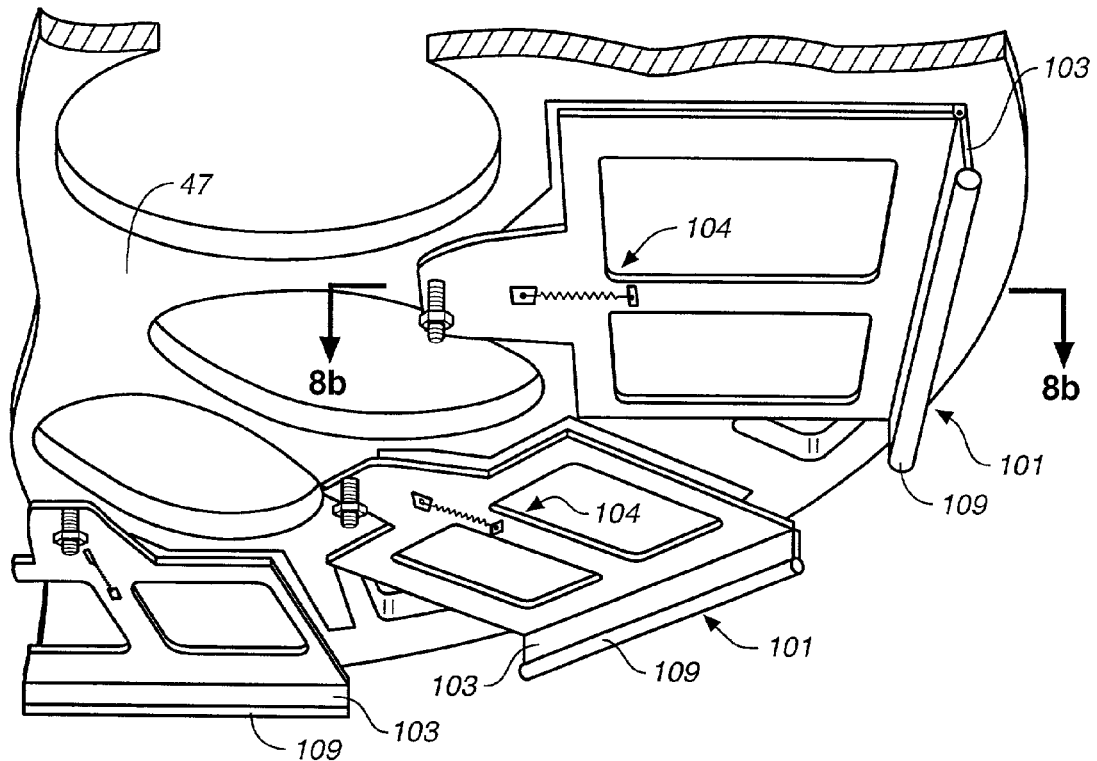
FIG._8a
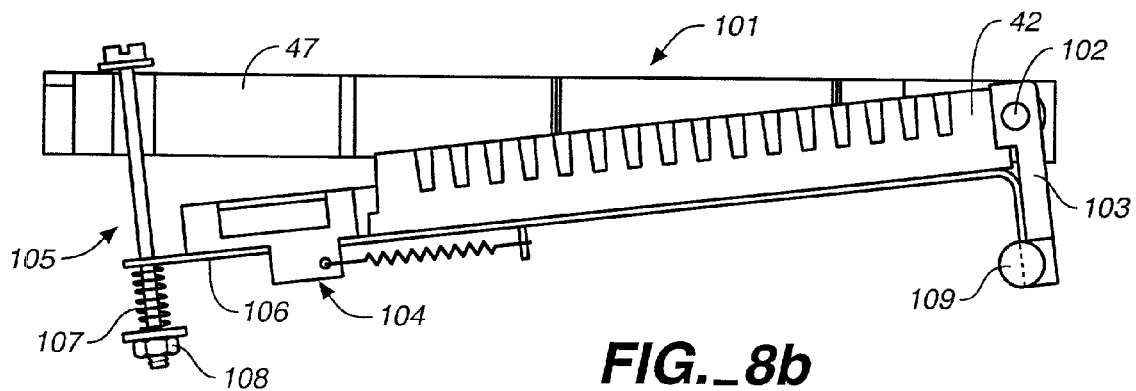
FIG._8b

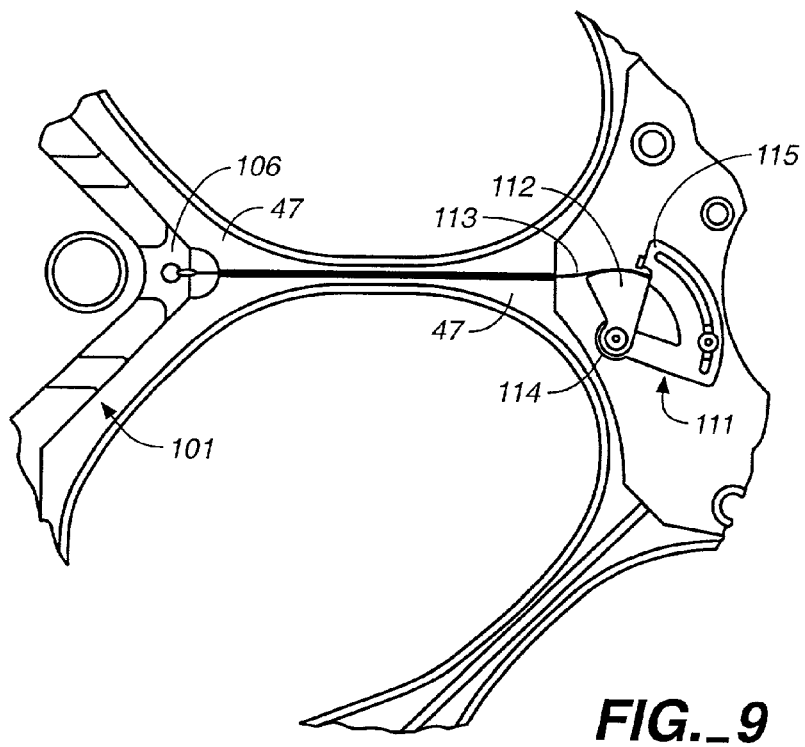
FIG._9
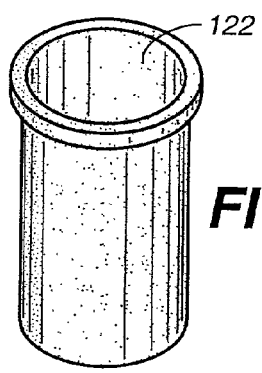
FIG._10c
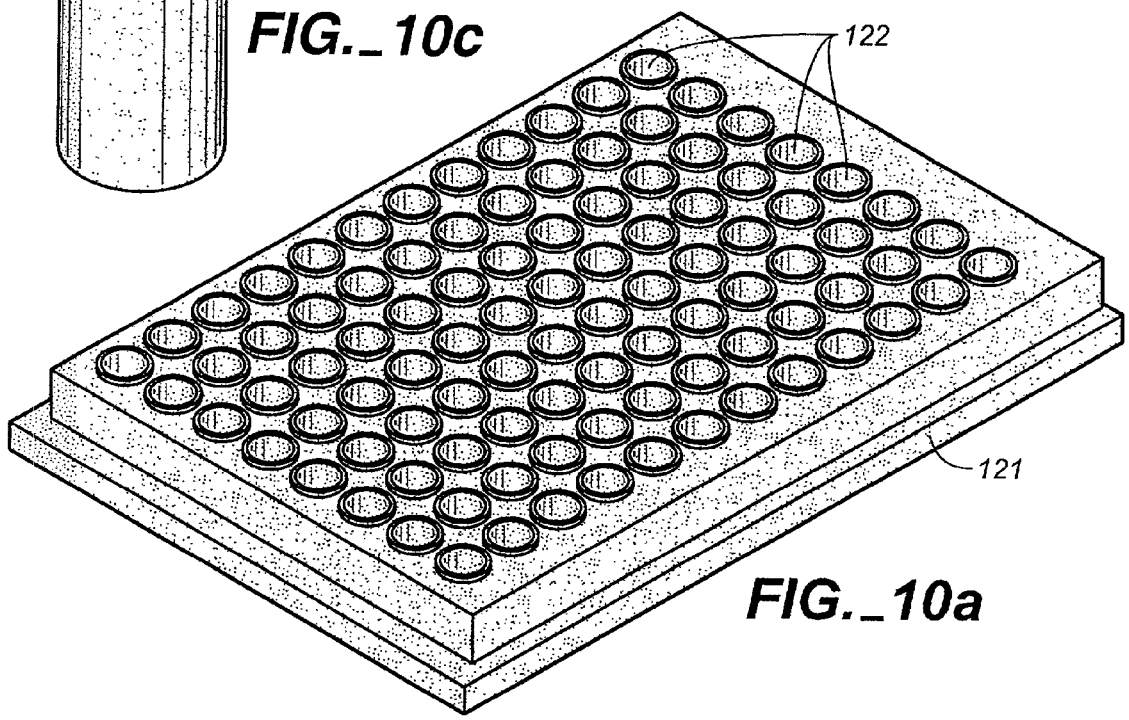
FIG._10a

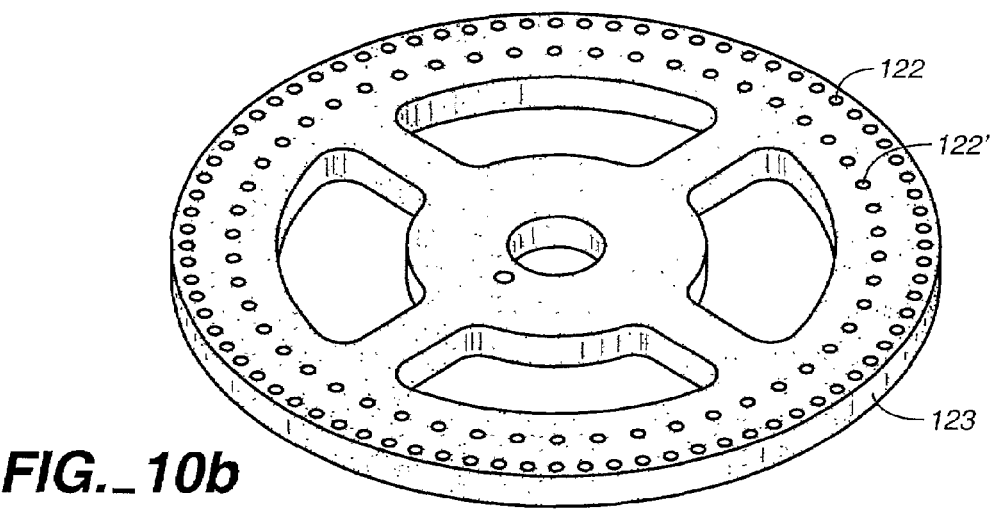
FIG._10b
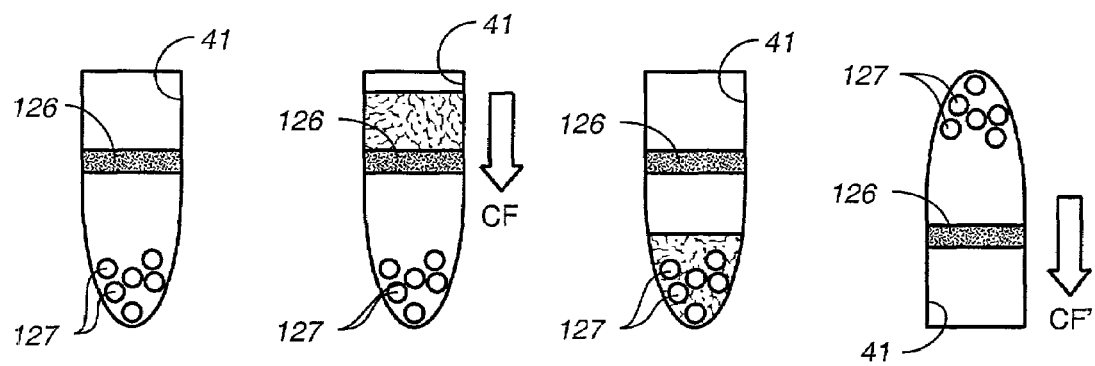
FIG._11a  FIG._11b  FIG._11c  FIG._11d
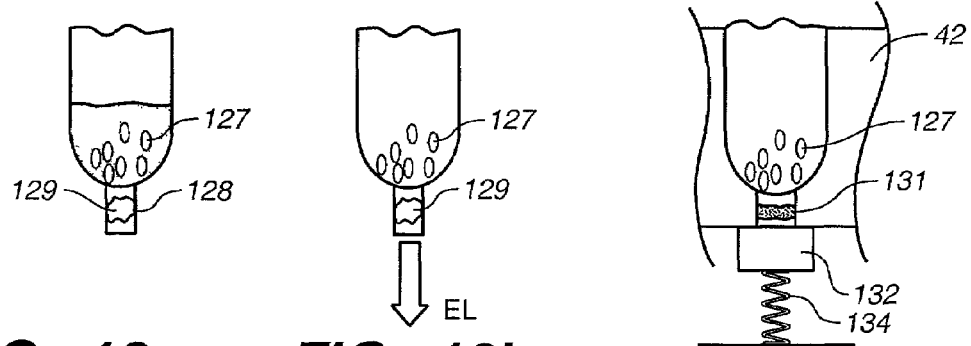
FIG._12a  FIG._12b  FIG._13

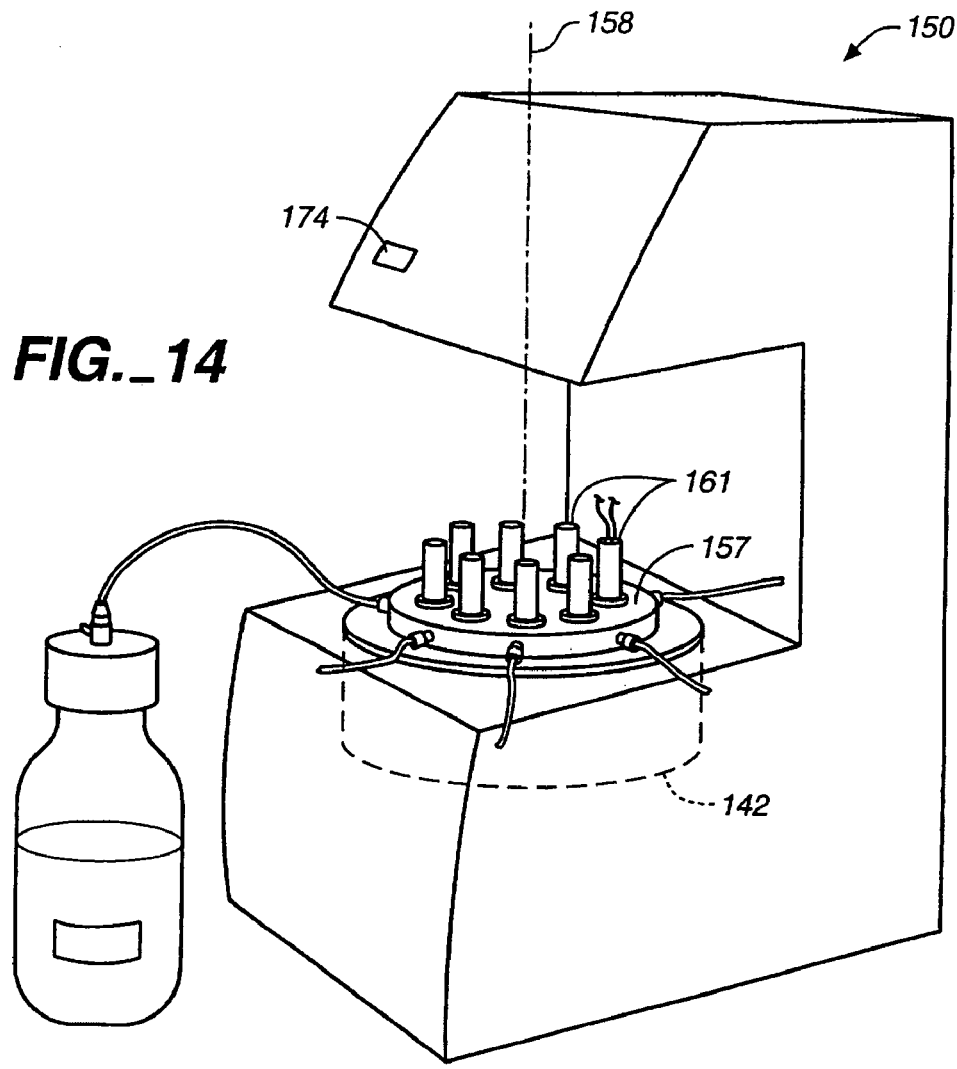
FIG._14
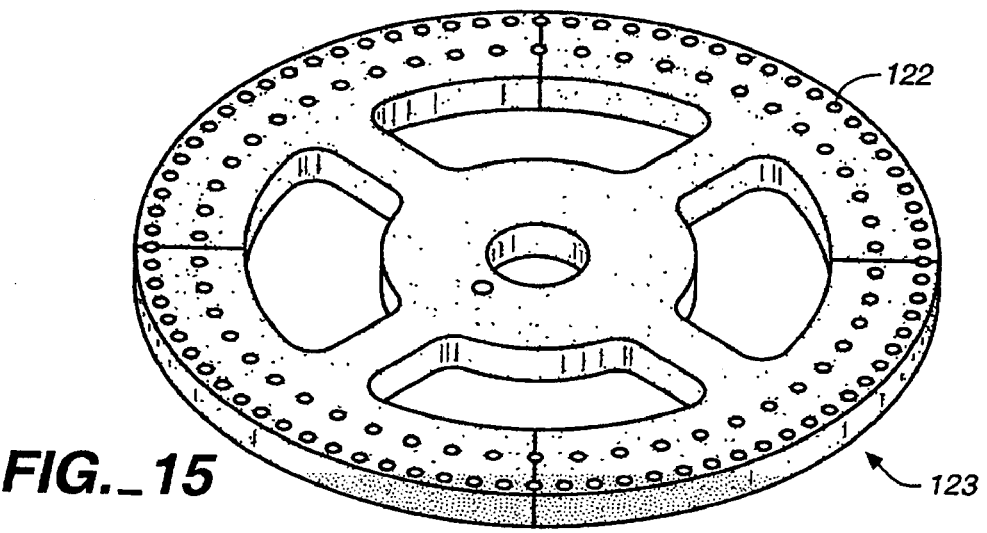
FIG._15

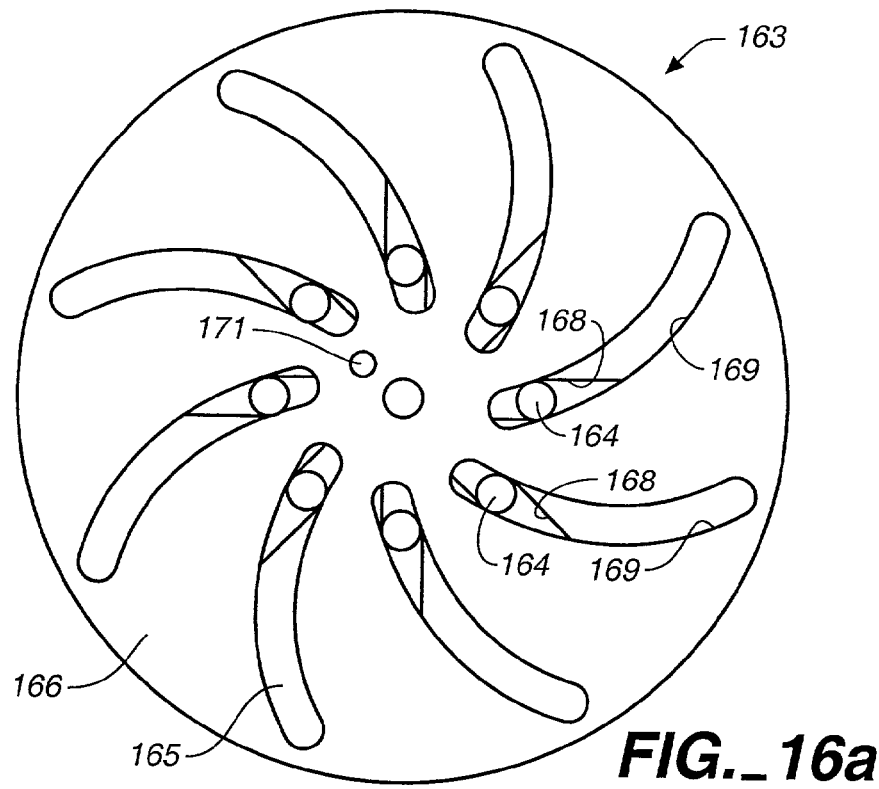
FIG._16a
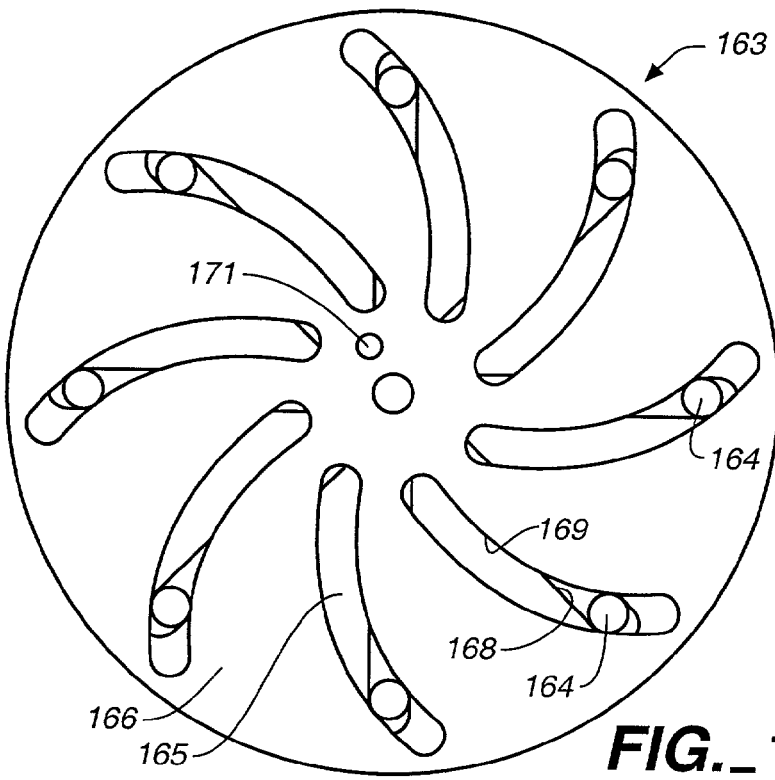
FIG._16b

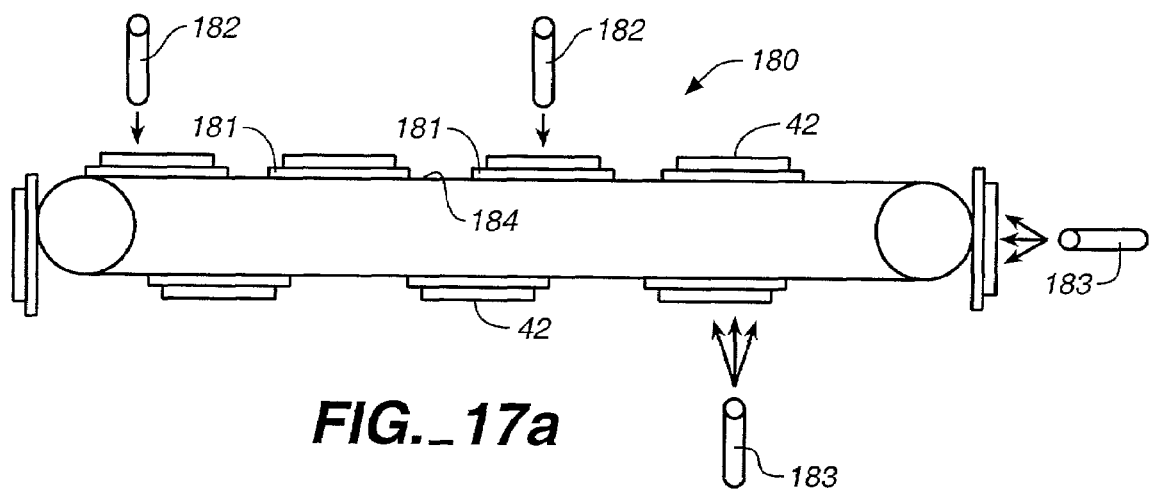
FIG._17a
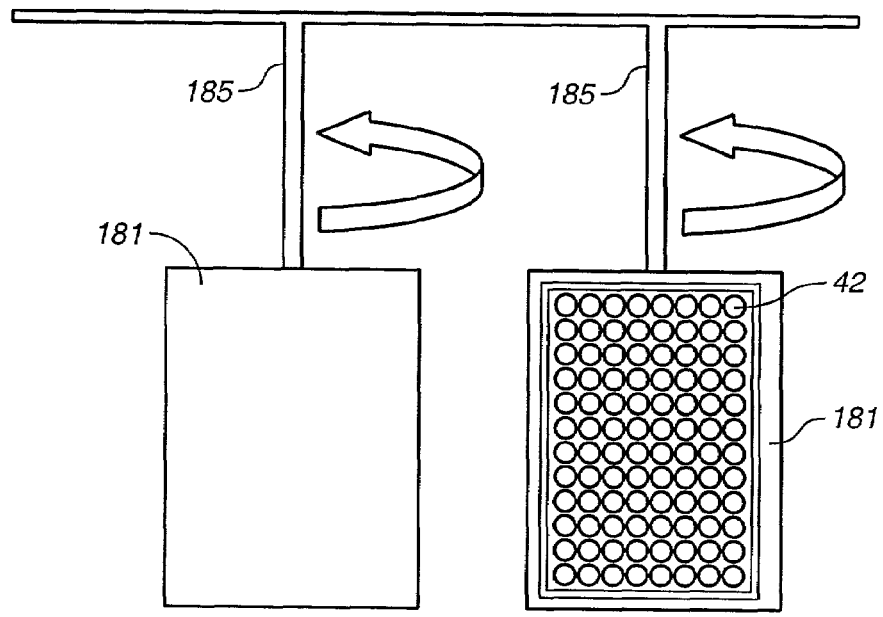
FIG._17b

OLIGONUCLEOTIDE SYNTHESIZER

RELATED APPLICATIONS

This application is a Continuation-in-Part of U.S. patent application Ser. No. 09/738,473, filed Dec. 13, 2000 now U.S. Pat. No. 6,663,832 and entitled Oligonucleotide Synthesizer, which claims priority to U.S. Provisional Patent Application Ser. No. 60/170,314 filed Dec. 13, 1999, entitled Oligonucleotide Synthesizer, the entire contents of which applications are incorporated herein by this reference.

This invention was made with government support under 2 R44 GM58981-02A1 awarded by the National Institutes of Health. The government has certain rights in the invention.

BACKGROUND OF THE INVENTION

1. Field of the Invention

The present invention relates to the field of devices and methods for chemical synthesis, analysis, and biological screening. More particularly, the present invention relates to a new and improved apparatus for high-throughput combinatorial synthesis of organic molecules, particularly nucleic acids.

2. Description of Related Art

Solid-phase synthesis of organic molecules is the method of choice for preparation of libraries and compound megaarrays, which are currently being applied for screening in the quest to find new drugs or pharmaceutical lead compounds, i.e., compounds which exhibit a particular biological activity of pharmaceutical interest. These leads can serve as a starting point for the selection and synthesis of a drug compound, which in addition to the particular biological activity of interest has pharmacologic and toxicologic properties suitable for administration to animals, including humans.

Several designs of instruments for combinatorial synthesis utilizing solid-phase synthesis are known. An exemplar of the prior art is U.S. Pat. Nos. 5,202,418 and 5,338,831, to Lebl et al., which each describe a method of performing multiple synthesis of peptides on a solid carrier. U.S. Pat. No. 5,342,585 to Lebl et al. describes an apparatus for multiple syntheses of peptides on solid support. U.S. Pat. No. 6,045,755 to Lebl, et al. describes an apparatus and a method for combinatorial chemistry synthesis. U.S. Pat. No. 6,121,054 to Lebl, corresponding to PCT International Publication No. WO00/25470, shows a method for separation of liquid and solid-phases for solid-phase organic synthesis. The entire contents of the above patents are incorporated herein by this reference.

Liquid removal by centrifugation was described and is the subject of several publications. See Christian Birr, Aspects of the Merrified Peptide Synthesis (Springer-Verlag, New York 1978; German Patent Application P 20 17351.7, G. 70 13256.8, 1970. These references describe the use of centrifugation for liquid removal from slurry of solid-phase particles in a concentric vessel equipped with a filtration material in its perimeter and spun around its axis.

SUMMARY OF THE INVENTION

In summary, one aspect of the present invention is directed to an apparatus for performing combinatorial-chemistry synthetic reactions including a reaction vessel for containing a combinatorial-chemistry synthetic reaction, a liquid dispenser for dispensing the liquid, and a liquid aspirator and an adjustment mechanism. The reaction vessel includes an ingress aperture allowing a liquid to enter into an interior of the vessel and an egress aperture for aspirating the liquid from the vessel. The liquid dispenser dispenses liquid through the ingress aperture. The liquid aspirator aspirates liquid through the egress aperture and includes a rotor for carrying the vessel and orbiting the vessel about an axis of rotation. The rotor is oriented generally in a horizontal plane and includes an adjustment mechanism for adjusting the angle of the vessel relative to the horizontal plane in response to the centrifugal force generated by orbiting the vessel about the axis of rotation. The dispenser Another aspect of the present invention is directed to an apparatus for dispensing liquids into a reaction vessel including a rotor, a liquid dispenser, and a controller. The rotor is mounted for rotation about a central axis and carries an array of reaction vessels along a circular path. The liquid dispenser includes a plurality of dispensing nozzles and is positioned above the rotor. The liquid dispenser is arranged for dispensing a liquid from each dispensing nozzle into a respective reaction vessel while the array of reaction vessels moves along the circular path past the liquid dispenser. The controller synchronizes the liquid dispenser and the array of reaction vessels such that the liquid dispenser dispenses liquid into the array of reaction vessels while the rotor is moving.

Another aspect of the present invention is directed to an apparatus for dispensing liquids including a plate and a plurality of dispensing nozzles. The plate includes a first circular array of reaction vessels and a second circular array of reaction vessels. The first and second circular arrays are concentrically arranged about a central axis. The plurality of dispensing nozzles is arranged in a circular pattern above the plate. Each dispensing nozzle is mounted for radial movement about the central axis.

Yet another aspect of the present invention is directed to an apparatus for chemical synthesis utilizing a plate having a plurality of reaction wells therein. The apparatus includes a plate holder, a first reagent dispensing nozzle, an inverting mechanism, and a second solution dispensing nozzle. The plate holder supports the plate in a plurality of positions. The first reagent dispensing nozzle is positioned to dispense a reagent into the plurality of reaction wells for chemical reaction with chemical moieties within the reaction wells when the plate holder supports the plate in an upright position. The inverting mechanism inverts the plate holder and moves the plate between the upright position and an inverted position. The second solution dispensing nozzle is positioned to dispense a solution into the reaction wells when the plate is inverted so that at least a part of the solution can drain by gravity from the reaction wells.

In general, it is an object of the present invention is to provide an apparatus for reagent delivery during solid-phase synthetic reactions while the dispensing head and rotor are moving and aligned.

Another object of the present invention is to provide an apparatus having an improved fluid delivery system and an improved centrifugal rotor assembly.

Another object of the present invention is to provide an apparatus for custom chemical synthesis that is easy to operate, has low initial cost, runs on convenient and easy-to-install consumables, and provides high-throughput combinatorial synthesis of organic molecules.

Yet another object of the present invention is to provide an apparatus for providing continuous liquid addition with respect to motion of the rotor and the fluid delivery system.

The accompanying drawings, which are incorporated in and form a part of this specification, illustrate embodiments of the invention and, together with the description, serve to explain the principles of the invention.

BRIEF DESCRIPTION OF THE DRAWINGS

FIG. 1 is a perspective view of an apparatus for high-throughput combinatorial syntheses of organic molecules in accordance with the present invention.

FIG. 2 is an enlarged perspective view of a portion of the apparatus shown in FIG. 1 showing a rotor assembly supporting a microtiter plate including a plurality of wells in accordance with the present invention.

FIG. 3 is an enlarged schematic view of the microtiter plate of FIG. 2 passing beneath nozzles of a liquid delivery system in accordance with the present invention.

FIG. 4 is partially-schematic, top-plan view of a portion of the apparatus of FIG. 1 having a modified liquid delivery system in accordance with the present invention.

FIGS. 5(a) and 5(b) are a graphs illustrating dispensing head motion along respective X-and Y-axis, of the apparatus of FIG. 1 in accordance with the present invention.

FIGS. 6(a) and 6(b) are graphs illustrating well motion along respective X-and Y-axis, of the apparatus of FIG. 1 in accordance with the present invention.

FIG. 7(a) is an enlarged, detailed, and exploded view of a nozzle and fluid connector of the apparatus shown in FIG. 1 in accordance with the present invention.

FIG. 7(b) is an enlarged, fragmented, and exploded view of a portion of the nozzle and fluid connector of FIG. 7(a).

FIG. 8(a) is an enlarged, partial perspective view of rotor assembly of FIG. 2.

FIG. 8(b) is a sectional view of a portion of the rotor assembly of FIG. 2 taken along line 8(b)-8(b).

FIG. 9 is a partial top plan view of the rotor assembly of FIG. 2 having a modified biasing mechanism in accordance with the present invention.

FIG. 10(a) is a perspective view of a modified microtiter plate including reaction wells similar to that shown in FIG. 2.

FIGS. 10(b), and 10(c) are perspective views of a rotor and an individual reaction well, respectively, similar to the reaction wells of FIG. 10(a).

FIGS. 11(a), 11(b), 11(c), and 11(d) are schematic views of a portion of a modified apparatus including filtering means located within modified wells in accordance with the present invention similar to those of FIG. 2.

FIGS. 12(a) and 12(b) are schematic views of wells in accordance with the present invention similar to those of FIG. 11.

FIG. 13 is a schematic views of a well in accordance with the present invention similar to those of FIG. 11.

FIG. 14 is a perspective view of a modified apparatus in accordance with the present invention similar to the apparatus shown in FIG. 1.

FIG. 15 is a perspective view of a modified rotor in accordance with the present invention similar to the rotor of FIG. 10(b).

FIGS. 16(a) and 16(b) are top plan views of a spiral translation mechanism of the apparatus of FIG. 14 in accordance with the present invention.

FIGS. 17(a) and 17(b) are schematic side and top plan views, respectively, of modified apparatus for high-throughput combinatorial syntheses of organic molecules in accordance with the present invention similar to the apparatus of FIG. 1.

DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

The present invention is directed to solid-phase, combinatorial chemistry synthesis of organic molecules. In particular, the apparatus of the present invention is particularly suited for solid-phase synthesis of oligomers using a centrifuge. Preferably, the apparatus of the present invention utilizes solid-phase particles such as microbeads for organic synthesis of oligomers. The apparatus of the present invention utilizes a centrifuge with a rotor for the step-wise addition and removal of solid and liquid phase solutions and the separation and removal of the solid-phase particles for synthetic reactions, as is described in U.S. Pat. No. 6,121,054 to Lebl entitled Method for Separation of Liquid and Solid Phases for Solid Phase Organic Synthesis, the entire contents of which is incorporated by this reference.

The oligonucleotides synthesized using the present invention are used in one of two ways. In one embodiment, and the beads comprising the oligonucleotides are directly dispersed on a bead array such as is generally described in PCT/US98/21193, PCT/US99/04473, PCT/US98/05025, PCT/US99/14387, and U.S. patent application Ser. Nos. 09/287,573, 09/256,943, 09/316,154, 09/425,633, 09/425,633, 60/161,148 for and 60/160,917, the entire contents of which are incorporated herein by this reference. Alternatively, the oligonucleotides may be cleaved from the synthesis support and added to different sets of beads for use in the bead arrays.

By way of introduction, in a preferred embodiment of the present invention is generally directed to the synthesis of nucleic acids. The terms "nucleic acid" or "oligonucleotide," and other grammatical equivalents herein, referred to at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989)), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. In addition nucleic acids include, "locked nucleic acids" such as those described in Koshkin et al., J. Am. chem. Soc. 120: 13252-3 (1998). All of these references are hereby expressly incorporated by reference.

The nucleic acids (sometimes referred to herein as oligonucleotides) can be synthesized using a variety of possible synthetic reactions. In a preferred embodiment, phosphoramidite chemistry is used, with enzymatic techniques and techniques based on photodeprotection useful as well. In addition, any number of nucleic acid analogs and labeled nucleic acids can be made and used. See for example Oligonucleotides and Analogs: A Practical Approach, Ed. F. Eckstein, IRL Press, 1991, hereby incorporated by reference in its entirety.

One should appreciate however that the present invention is similarly applicable to other chemical protocols having similar functional steps. For example, components of the present invention can be applied to appropriate liquid-phase, combinatorial chemistry synthesis protocols, to other solid-or liquid-phase chemical protocols, or to any combination thereof.

"Protein" as used herein includes proteins, polypeptides, and peptides. The protein may be made up of naturally occurring amino acids and peptide bonds, or synthetic peptidomimetic structures. The side chains may be in either the (R) or the (S) configuration. In a preferred embodiment, the amino acids are in the (S) or L-configuration. If non-naturally occurring side chains are used, non-amino acid substituents may be used, for example to prevent or retarded in vivo degradations. Proteins can be synthesized using the methods and apparatus of the present invention using standard techniques.

One aspect of the present invention is directed to the use of plates, such as microtiter plates, which support and contain the solid-phase for solid-phase synthetic reactions. In particular, the microtiter plates house beads that are used as the solid-phase. By "particle" or "microparticle" or "nanoparticle" or "bead" or "microbead" or "microsphere" herein is meant microparticulate matter. As will be appreciated by those in the art, the particles can comprise a wide variety of materials depending on their use, including, but not limited to, cross-linked starch, dextrans, cellulose, proteins, organic polymers including styrene polymers including polystyrene and methylstyrene as well as other styrene co-polymers, plastics, glass, ceramics, acrylic polymers, magnetically responsive materials, colloids, thoriasol, carbon graphite, titanium dioxide, nylon, latex, and TEFLON® may all be used. "Microsphere Detection Guide" from Bangs Laboratories, Fishers, Ind., is a helpful guide.

By way of introduction, combinatorial chemistry synthesis protocols prescribe the sequential addition of building blocks to intermediate, partially synthesized, compounds in order to synthesize a final compound. These protocols are, generally, divided into liquid-phase protocols and solid-phase protocols. In liquid-phase protocols, final compounds are synthesized in solution. Partially synthesized, intermediate compounds are separated from spent reagents between building block addition steps by known means, such as precipitation, fractionation, and so forth. In solid-phase synthesis, final compounds are synthesized attached to solid-phase supports that permit the use of simple mechanical means to separate partially-synthesized intermediate compounds between synthetic steps. Typical solid-phase supports include microbeads having diameters from approximately 30 microns to 300 microns to which intermediate compounds covalently attach.

Solid-phase combinatorial synthesis typically proceeds according to the following steps. In a first step, reaction vessels are charged with a solid-phase support, typically a slurry of microbeads suspended in a solvent. These microbeads are then preconditioned by incubating them in an appropriate solvent, and the first of the plurality of building blocks or a linker moiety is covalently linked to the microbeads. Subsequently, a plurality of building block addition steps are performed, all of which involve repetitive execution of the following or similar sub-steps, and in a sequence chosen to synthesize a desired compound. First, a sufficient quantity of a solution, which contains the building block moiety selected for addition, is dispensed into the reaction vessels so that the building block moiety is present in a molar excess to the intermediate compound present in the reaction vessel. A sub-step reaction is triggered and promoted by activating reagents and other reagents and solvents, which are also added to the reaction vessel. The reaction vessel is then incubated at a controlled temperature for a time, typically between 5 minutes and 24 hours, sufficient for the building block addition reaction to go to substantial completion. Optionally, during this incubation, the reaction vessels can be intermittently agitated or stirred. Finally, in a last sub-step of building block addition, the reaction vessel containing the solid-phase support with attached intermediate compound is prepared for addition of the next building block by removing the spent reaction fluid and thoroughly washing and reconditioning the solid-phase support. Washing typically involves three to seven cycles of adding and removing a wash solvent. Optionally, during the addition steps, multiple building blocks can be added to one reaction vessel in order to synthesize multiple compounds attached to one solid-phase support, or alternatively, the contents of separate reaction vessels can be combined and partitioned in order that multiple compounds can be synthesized in one reaction vessel with each microbead having only one attached final compound (this is sometimes referred to as a "split and mix" synthesis). After the desired number of building block addition steps, the final compound is present in the reaction vessel and attached to the solid-phase support. The final compounds can be utilized either directly attached to their synthetic solid-phase supports, or alternatively, can be cleaved from their supports. In the latter case, the linker moiety attaching the compound to the solid-phase support is cleaved in a variety of ways, and the final compound, or library of compounds is extracted from the reaction vessel into a liquid phase.

An exemplary solid-phase combinatorial protocol is that for the synthesis of peptides attached to MBHA resin, which proceeds according to Lam et al., 1991, "A new type of synthetic peptide library for identifying ligand-binding activity," Nature 354: 82-84. Another exemplary protocol is that for the synthesis of benzodiazepine moieties, which proceeds according to Bunin et al., 1992, "A general and expedient method for the solid-phase synthesis of 1,4-benzodiazepine derivatives," J. Amer. Chem. Soc., 114: 10997-10998. Exemplary building blocks and reagents are nucleic acids, amino acids, other organic acids, aldehydes, alcohols, and so forth, as well as bifunctional compounds, such as those given in Krchnak et al., 1996, "Synthetic library techniques: Subjective (biased and generic) thoughts and views," Molecular Diversity, 1: 193-216.

In view of the large potential numbers of final compounds in combinatorial libraries, it is advantageous that at least some manipulations needed by the synthetic protocols be assisted or performed automatically. In view of the exemplary protocol described, an automated apparatus for combinatorial chemistry synthesis advantageously includes facilities for handling fluids, for manipulating reaction vessels, and for storage of reagents and building blocks. Advantageous facilities for fluid handling include: facilities to accurately dispense solutions and slurries which contain building blocks, solid-phase substrates, reagents, and/or solvents into the reaction vessels; facilities to rapidly and repetitively add wash solvents into the reaction vessels; and facilities to rapidly and accurately remove fluid phases from the reaction vessels leaving behind the solid-phase supports within the reaction vessels with respective attached intermediate compounds. Facilities for manipulating reaction vessels and reaction vessel arrays include: facilities to move reaction vessels and reaction vessel arrays between various stations; facilities for time and temperature controlled incubation of reaction vessels and reaction vessel arrays; and optionally facilities for agitation of reaction vessels during incubation. Each such protocol typically uses many building blocks, perhaps hundreds, a several activating and other reagents, and one or two work solvents. Accordingly, there are storage facilities for: a large number of building blocks solutions, typically 300 or more building blocks solutions or more preferably as many as 600 or more building blocks solutions stored, for example, in arrays; preferably 6 or more preferably 12 or more reagents in larger quantities than for building block solutions; and preferably 3 or more preferably 6 or more of even larger quantities of wash solvents.

The apparatus of the present invention advantageously permits simultaneous, parallel processing to occur during solid-phase synthesis in order to achieve high synthesis throughput. This is achieved because the design of the apparatus includes a few standardized physical sizes and layouts having a modular nature. Thereby, processing resources can be simultaneously applied to multiple protocols in many reaction vessels which can be sized to achieve high throughput.

Preferred materials for all elements of the present invention in contact with the synthetic addition reactions, in particular the reaction vessels, must resist the harsh reagents, solvents, and reaction conditions likely to be encountered in the various protocols. In the following detailed description, when solvent resistance is specified and particular materials are not specified, the following exemplary general purpose solvent resistant materials can be used: TEFLON®, plastics including polypropylene, or glass, among others.

Turning now to the drawings, FIG. 1 illustrates one embodiment of an apparatus 40 according to the present invention that is advantageous for high throughput, multi-protocol combinatorial syntheses. Apparatus 40 is adapted for synthesizing oligomers in each of a plurality of reaction vessels 41 (FIG. 2) which are disposed in arrays, such as the rectangular array of reaction vessels or wells 41 disposed in microtiter plate 42 (FIG. 2). Apparatus 40 generally includes a support enclosure 45, a rotor assembly 46 (FIG. 2) for supporting one or more microtiter plates 42, an enclosed support surface 49, and a liquid delivery system 50. Support enclosure 45 provides mechanical support for rotor assembly 46, support surface 49 and liquid delivery system 50. The support enclosure 45 illustrated in FIG. 1 is approximately 28"×30"×72" (71 cm×76 cm×183 cm. One should appreciate that the dimensions may vary in order to provide a width, depth and height sufficient support a sufficient number of work stations, tools, and reaction vessel arrays to achieve the desired level of synthetic throughput.

Rotor assembly 46 is rotatably supported by support enclosure 45 below support surface 49 and rotates about a centrifugal axis 51 which extends substantially orthogonal to support surface 49. Liquid delivery system 50 includes a reagent delivery station or reagent dispenser 52 and a bulk liquid delivery system or bulk dispenser 53 supported on support surface 49. Reagent dispenser 52 is a multi-channel dispenser that is capable of simultaneously delivering a plurality of different liquids to corresponding different sets of wells 41 of microtiter plate 42. Reagent dispenser 52 is also capable of sequentially delivering a plurality of different liquids to wells 41 of microtiter plate 42. Reagent dispenser 52 is fluidly connected to tubing 55 which, in turn, is connected to storage bottles 56. Tubing 55 and storage bottles 56 are pressurized in order to deliver liquids to reagent dispenser 52 at a controlled pressure. Alternatively, one or more suitable pumps can be connected to the tubing in order to deliver desired liquids from one or more of the bottles to the reagent dispenser at a controlled pressure. In contrast, bulk dispenser 53 is provided to dispense wash-solvent into the entire array of wells 41 of microtiter plate 42 at one time and may be utilized to implement a plurality of washing steps. Bulk dispenser 53 is similarly connected to tubing 58 which, in turn, is connected to a suitable storage bottle and/or pump located below support surface 49. Although the illustrated embodiment shows the storage bottles located within support enclosure 45, one should appreciate that the position of the storage bottles and/or pumps may vary. For example, the bottles and/or pumps may be located external to support enclosure 45.

Dispensers 52 and 53, as well as other components needing more frequent attention by an operator, are preferably disposed above support surface 49, while facilities needing less frequent attention, such as rotor assembly 46, a bulk liquid pump and other components requiring less maintenance, are preferably disposed below support surface 49. The present invention is adaptable to other distribution of processing equipment above and below the support surface. Alternatively, one liquid handling work station can be adapted to both dispense and aspirate work solvents. For example, a bulk liquid dispenser can be configured for operation in a dispensing mode and in a suction or aspiration mode.

The apparatus shown in FIG. 1 includes a sub-enclosure 54 supporting a drum 142. Rotor assembly 45 is contained within drum 142. Drum 142 is adapted for retaining an inert atmosphere within a portion of support enclosure 45 thus maintaining an inert atmosphere in which synthesis takes place. Sub-enclosure 54 is preferably ventilated to contain vapors that escape from drum 142, The vapors are ventilated out from sub-enclosure 54 via an exhaust duct. Sub-enclosure 54 is generally of a rectangular or cubical shape and preferably includes glass or plastic surfaces which are resistant to the harsh reagents and solvents used during synthesis procedures. Preferably, sub-enclosure 54 includes a slidable access panel 57 which allows an operator ready access to plate 42 and the various components located above support surface 49. Sub-enclosure 54 contains liquid dispensers 52 and 53 as well as other work stations that must be manipulated within a controlled environment. The sub-enclosure is charged with a heavier than air inert gas, such as argon and/or other inert gases in order to maintain unsealed reaction vessels or open wells 41 in an inert atmosphere.

Turning now to the liquid delivery system, conventional synthesizers dispense liquid into individual wells of a microtiter plate utilizing a two axis X-, Y positioning system for aligning liquid delivery nozzles with respective wells while a centrifuge is at rest. These systems do find use in some embodiments of the present invention. However, for high-throughput systems, this approach is relatively slow because the rotor assembly or centrifuge must be stopped before liquid delivery can proceed, thus disadvantageously increasing cycle time and reducing throughput.

Accordingly, in a preferred embodiment, reagent delivery dispenser 52 of the present invention is capable of addressing each well 41 individually while microtiter plate 42 is moving while rotor assembly 46 is spinning about centrifugal axis of rotation 51. This is possible, in part, because a reagent dispenser head 60 of reagent dispenser 52 is mounted in a reagent dispenser translation frame 62 in order to move with respect to support surface 49. Translation frame 62 is configured to move reagent dispenser head 60 along three substantially orthogonal axes with respect to the support surface 49. In particular, X-, Y-, and Z-linear actuators move dispenser head 60 along respective X-, Y-, and Z-axes thereby allowing reagent dispenser 52 to address each well 41 individually by synchronizing the motion of dispenser head 60 with the speed of rotor assembly 46 during centrifugation. Reagent dispenser 52 may be further synchronized to address each well 41 individually by synchronizing the rate of and duration of liquid delivery with the speed of rotor assembly 46. A reagent dispenser with such a configuration generally requires fewer parts than prior devices because the design of the present invention takes advantage of the motion of the microtiter plates and the centrifuge along a fixed path. The X-, Y-, and Z-linear actuators are synchronized to follow the fixed arcuate path of microtiter plate 42 as it spins with rotor assembly 46. One should appreciate that a fourth axis, a θ axis, must be included in the event that reagent dispenser 52 is configured to simultaneously address two or more wells 41 in microtiter plate 42 while rotor assembly 46 is in motion.

In particular, wells 41 are filled as they pass beneath a respective nozzle 65', 65" (shown schematically in FIG. 3) of the reagent delivery head which is activated so that liquid delivery is synchronized with microtiter plate 42 movement along the fixed circular path of rotor assembly 46. Accordingly, reagents can be delivered to individual wells 41 as needed without bringing rotor assembly 46 and microtiter plate 42 to a complete halt. Similarly, the need to move delivery nozzles 65 can be minimized or eliminated. Multiple reagents can be dispensed simply by adding additional nozzles in series. For example, a two channel delivery configuration is shown schematically in FIG. 3 in which one nozzle 65' may fill one set of wells of a microtiter plate with a first reagent R1 and a second nozzle 65" may fill another set of wells with a second reagent R2 while microtiter plate 42 remains in motion, as indicated by arrow A.

Preferably, each column of wells is addressed in parallel. For example, to address an 8×12 well microtiter plate, a set of 8 nozzles, in a manner analogous to an ink-jet print head, can be used to address all 8 wells of a column within a microtiter plate in parallel, that is simultaneously. Delivery would be made to each well in a column as needed. Sets of nozzles positioned in series allow the simultaneous delivery of multiple reagents, as shown in FIG. 3. Alternatively, single nozzles can be used.

Such a configuration is conducive to multiple channel delivery of reagents to a microtiter plate having either 96 wells, 384 wells, or more wells arranged in an array on a microtiter plate. In the illustrated embodiment, reagent dispenser head 60 includes an array of forty nozzles arranged on five cartridges 66 (FIG. 1), wherein each cartridge 66 includes eight downwardly directed nozzles (not shown in FIG. 1) arranged in a linear fashion. Such a multiple channel delivery allows the simultaneous delivery of five different reagents, for example A, C, G, and T bases and an activator into respective wells 41 in a similar manner that is illustrated in FIG. 3. Each nozzle is provided with an electric solenoid valve which is capable of liquid delivery in durations of less than one to two milliseconds.

As noted above, conventional synthesizers dispense liquid into individual wells of a microtiter plate utilizing a two axis XY-positioning system for aligning liquid delivery nozzles with respective wells while a centrifuge is at rest. For example, current methods for dispensing liquids into microtiter plates via automation or robotics generally utilize motion systems acting orthogonally with respect to the orientation of wells within the microtiter plate. The X- and Y-axes of a conventional liquid handling robot correspond to the rows and columns of wells within a microtiter plate. Generally a conventional XY-motion system (or an XYZ-motion system in the case that a vertical axis is required for the aspiration of liquids from a microtiter plate) will manipulate a liquid handling head over a deck composed of an array of microtiter plates. The liquid handling head is typically composed of a linear array of nozzles, connected by tubing to syringe pumps or pressure backed bottles to allow for the accurate and precise transport of liquid either from a source microtiter plate to a destination microtiter plate or the accurate and precise dispensing from bulk sources into microtiter plates.

Other types of conventional liquid handling devices may not be arranged orthogonally in a convenient manner for liquid handling, depending upon physical geometry dictated by other requirements and designs. One example of this is liquid delivery to a radial arrangement of microtiter plates, as in a microtiter centrifuge. In this arrangement, microtiter plates are located within a circular rotor such that the each long side of a microtiter plate is normal to radial lines at regular intervals, at a distance from the center sufficient to accommodate the number of plates desired within the rotor. The circular rotor is driven by a stepper motor, capable of acceleration, velocity and positional accuracy performance desired for centrifuge operations. Within this arrangement, conventional orthogonal access must be made by halting the circular rotor such that a conventional XY-driven dispenser array may access all the wells within the microtiter plate only while the rotor is halted, that is while the rotor is at rest. For accessing a 96 well microtiter plate, consisting of an 8×12 array of wells, only a conventional X-positioning actuator would be required. For a 384 well microtiter plate, consisting of a 16×24 array of wells, a conventional X-axis positioning device with a discreet two position Y-actuator is sufficient. For densities beyond 384 wells, a Y-position actuator of greater resolution such as a linear ball screw is desirable. This conventional arrangement is satisfactory for accessing the microtiter plates in a static condition, that is when the rotor is at rest. However, the microtiter plate must be immobile while the liquid delivery head is maneuvered over the plate along the X-axis of conventional devices.

The apparatus of the present invention precisely controls dispensing valves within reagent dispenser 52 to allow dispensation of liquids in to wells 41 without stopping dispenser head 60. This is accommodated by utilizing a real-time control architecture of the dispensing valves, that is by providing both accurate and precise control of the solenoid valve of each nozzle 65 to valve states, that is initiating a change in state, to within 10-15 milliseconds. This allows the dispensing head to continue moving at a constant rate while the dispensing valves are actuated on demand as they pass over individual wells.

In another embodiment of the present invention, the apparatus is capable of dispensing liquid into the wells of the microtiter plate without the need to halt either the rotor or the reagent dispenser head 60. Rotor assembly 46 of the present invention is driven by a compact, powerful stepper motor with high resolution (+/−4000 quadrature counts/revolution). The motor is capable of high acceleration and deceleration rates, velocities up to 4000 RPM, and positioning resolution of +/−0.2 degrees. Active braking of the rotor assembly can also be utilized to further assist in decelerating the rotor assembly. The motor is controlled by a real time, (determinately behaving) controller. In one embodiment of the present invention, active breaking during the centrifugation process can be done.

With reference to FIG. 4, reagent dispenser head 60 is mounted in a positioning mechanism 67 instead of an XYZ-translation frame. Positioning mechanism 67 links a small head positioning motor (a stepper motor similar in form to the rotor motor) via a pivot to a pivot linkage and a suitable bearing mechanism. This positioning motor, through less than 180 degrees of rotation, maneuvers reagent dispenser head 60 such that its array of nozzles (shown schematically as nozzles $65^{A1}$, $65^{C1}$, and etc., in FIG. 4) match orthogonally to the array of wells $41^{A1}$, $41^{B1}$, etc., within microtiter plate 42 as both dispenser head 60 and plate 42 are in constant synchronized motion. A motor shaft 70 is connected to a circular arm 69 that an effective length Ld which measures approximately 5 mm from the center of motor shaft 70 to the center point of a pivot 71 on its opposite end. The motion of this pivot point (Xd, Yd) is described by the formulas:

$$Xd = COS(\theta) * Ld$$

$$Yd = SIN(\theta) * Ld$$

where θ is the motor angle and Ld is the length of the arm, as is indicated in FIG. 4.

Pivot point 71 is connected to a linear bearing via a linkage arm 74 that translates the rotational motion of the motor and arm into a linear motion, along the Y-axis, as indicated by arrow Y in FIG. 4, and in line between the central axis of the rotor and dispenser motor's axis of rotation about motor shaft 70. The location of this linkage pivot point (Xl, Yl) is determined as follows:

$$Xl = 0$$

$$Yl = SQRT((Lb+Xd)*(Lb-Xd))$$

wherein the X component is constrained to 0; SQRT is to take the square root of ( ); and Lb is the length of the bearing linkage arm.

Given that correct values are established for the lengths of the various linkage components and the locations for centers of rotation of the head positioning mechanism motor and the rotor assembly, the criteria for establishing alignment between the dispenser nozzle arrays and microtiter wells is aligning the angle of rotation of the rotor to the angle of the linkage arm. This is determined by:

$$\theta L = ASIN(Xd/Lb)*(180/\pi)$$

$$\theta R = \text{Given by motor commanded position}$$

Wherein θL is the linkage arm angle in degrees, relative to the linear bearing pivot point; π is the value 3.14159. The location of the A1 nozzle position relative to the bearing pivot point is determined by:

$$Xn = Nv * Xd/Lb$$

$$Yn = Yl + (Nv * COS(ASIN(Xd/Lb)))$$

wherein: Xn is the A1 X-axis nozzle location relative to the bearing pivot; Yn is the A1 Y-axis nozzle location relative to the bearing pivot; Nv is the distance between the A1 axis nozzle location and the bearing pivot point (the hypotenuse of the triangle formed by Xn and Yn).

The location of well A1 in a microtiter plate within the rotor, in the coordinate system of the dispenser head is determined by:

$$Xr = SIN(\theta L * \pi/180) * Rv$$

$$Yr = ABS(Ya - (COS(\theta L * \pi/180) * Ya)) + Ya$$

wherein: Xr is the A1 X-axis position relative to the origin at the dispenser drive motor center of rotation; Yr is the A1 Y-axis position relative to the origin at the dispenser drive motor center of rotation; Ya is the measured distance from the rotor center to the center of well A1 along the Y-axis; Rv is the distance between the rotor center point and the A1 well position (The hypotenuse formed by Xr and Yr); and ABS( ) is to take the absolute (non-negative) value of the number evaluated.

Evaluation of the preceding formulas as a system with variable data provided that reflects the dimensions associated with accommodating eight 384 well microtiter plates (128 mm×84 mm) within a rotor of 560 mm diameter yields the motion profiles illustrated in FIG. 5. The motion of well A1 in a 384 well microtiter plate is illustrated in FIG. 6.

In liquid delivery operation, the start point is properly synchronized, as accomplished by using feedback control of plate registration using a laser or other suitable means. For example, in one embodiment of the present invention, an edge detecting diode laser sensor tied to a high speed interrupt input in the motor controller, and the relative velocities of the motors are matched. With reference to FIG. 4, because a continuous path system is established, the reagent dispenser head 60 may traverse over microtiter plate 42, with both components in constant motion, such that accurate alignment between the nozzle array and array of microtiter plate wells will exist at nearly regular intervals. During these intervals any one of the dispensing valves, when called upon programmatically from the real time controller, can open and dispense liquid into a corresponding well, and close before the nozzle and the well travel out of alignment. Once a pass over a plate has been made, the head can move back to its start position with a rotation of less than 180 degrees while the rotor continues in the same direction bringing the next microtiter plate toward the position where dispensation can begin for the next microtiter plate. In the case of microtiter plate densities greater than 96 wells, successive passes of the rotor may be made, shifting the dispenser in the Y-axis before the beginning of each pass.

Advantageously, such a configuration utilizing positioning mechanism 67 increases the efficiency and throughput of a microtiter plate based centrifuge synthesis system and provides for an efficient dispensing configuration on a liquid handling system that utilizes radial geometry for organizing and moving microtiter plates. This embodiment of the present invention provides for a means of continuous liquid addition with respect to synchronized motion of the rotor and dispenser. This embodiment provides for complete orthogonal access to microtiter plates of a rotor assembly utilizing only two drive motors and without motion control algorithms that would be associated with an XYZθ system.

Although only one reagent dispenser head 60 is illustrated in FIG. 1, apparatus 40 may be provided with multiple reagent dispenser heads. For example, a second reagent dispenser head may be provided diametrically opposed to bulk fluid dispenser 52, that is to the right side of support surface 49 as viewed in FIG. 1. One should appreciate that the apparatus may include one, two, three or more reagent dispenser heads and still fall within the scope of the present invention.

Additionally, a supplemental reagent dispenser head may be provided to serve as a spare. For example, if one nozzle or one cartridge of reagent dispenser head 60 is malfunctioning, an operator may remove it from translation frame 62 and move it to a maintenance station 80 (FIG. 1). Maintenance station 80 is located above support surface 49 and remote from the other major components of apparatus 40, namely the rotor assembly and the bulk fluid dispenser. The operator may then disconnect the fluid lines and reconnect the lines to the supplemental regent dispenser head and, in turn, install the supplemental head on translation frame 62. Accordingly, the apparatus can continue to operate while the malfunctioning dispenser head is serviced, reconditioned, or replaced.

The reagent dispenser head may take a variety of alternative forms and fall within the scope of the present invention. A variety of delivery techniques for the delivery of reagents to the microtiter plate wells may be used, including inkjet and piezo techniques. For example, the reagent dispenser head of the present invention may include self-contained cartridges. Typically, solutions such as A, C, G, and T bases and activators are prepared in large volumes kept in large containers. This is because the solution must be made fresh and cannot be stored longer than a couple of days. Typically, each solution is prepared with crystalline materials and liquid materials separated from one another. A cartridge in accordance with the present invention similarly includes crystalline and liquid materials separated by suitable means such as a membrane. The cartridge membrane is pierced by suitable means and the materials mix together to form the solution.

The regent dispenser head and nozzles may include various types of fluid connections. Conventional tubing types are relatively soft and compliant and are not well-suited for harsh organic solvents. In contrast, tubing that is made to withstand harsh organic solvents is generally not soft and compliant, but is rather stiff in nature being more like a plastic than a rubber product. Typically, a small barbed fluid fitting is used in conjunction with a relatively soft and flexible tubing. The tubing generally slips over a barbed end and stretches to create a seal at the edge of barb, provided that the tubing is sized correctly to the barbed fitting.

In a preferred embodiment, a barbed fitting 90 (FIGS. 7(a) and 7(b)) of the present invention has a fluid interface that is not dependent upon conventional soft tubing. Instead, a "quick-connect" barbed fitting utilizes a spring loaded collar force to provide a compression fit around the end of the fitting. See FIG. 7(a). In particular, the fluid delivery system of the present invention utilizes a TEFLON® fitting or port 91 designed to accept a barbed end 92 of fitting 90 for a certain distance, but not the complete length of barbed end 92. The port 91 is designed with a chamfer 94 (FIG. 7(b)) to help guide and center port 91 on a cone shaped barb 95 on barbed end 92. Barbed end 92 is held in place by a spring 96 that applies a constant pressure to nozzle 65 and barbed end 92 biasing it into TEFLON® port 91 when nozzle 65 is inserted into cartridge 66 (FIG. 1) This configuration provides a constant pressure which maintains barbed end 92 within port 91 because the constant pressure is greater than any internal fluid pressure that will be generated within the reagent delivery system, which is generally less than 10 psi and preferably approximately 3 psi. Because the TEFLON® has a low hardness, TEFLON® port 91 deforms slightly and conforms to the shape and angle of barbed end 92. Over time the TEFLON® will creep slightly and, because the spring is applying constant pressure, will maintain and even improve the seal of barbed fitting 90. Advantageously, this configuration offers greater ease of assembly and disassembly. An operator merely needs to compress spring 96 and pull barbed end 92 out of TEFLON® port 92 to disconnect the fitting removing guide members 97 from alignment holes in cartridge 66 (FIG. 1) and remove nozzle 65 from the cartridge. To replace nozzle 65, an operator merely needs to insert nozzle end 98 into a corresponding nozzle aperture in cartridge 66, compress spring 96, and then align guide members 97 with corresponding alignment holes in cartridge 66.

The barbed fitting of the present invention is purely suited for connecting a barbed type tube coupler to a manifold or other fluid handling device without using flexible tubing. Such a configuration also promotes simplified manifold design suitable for micro-fluid applications that require valves having a barbed fitting. Furthermore, such as configuration allows barbed fittings to be used in applications which utilize harsh solvents.

Turning now to centrifugation and liquid removal, a rotor assembly typically is activated to centrifugate microtiter plates in a fixed angle with respect to the rotor and with respect to vertical. Precise separations may be achieved by controlling the amounts of liquids, the angle of the microtiter plate, the speed, and the duration of rotation. Previous centrifugal synthesizers utilized rotor that held microtiter plates at a fixed angle, as is described in U.S. Pat. No. 6,045,755 to Lebl et al., the entire contents of which is incorporated by this reference. In contrast, rotor assembly 46 of the present invention dynamically alters the angle of microtiter plate 42 during centrifugation. Rotor assembly 46 allows the angle of microtiter plate 42 to dynamically adjust between different synthesis processes but maintains microtiter plate 42 at a fixed, substantially horizontal position with respect to rotor assembly 46 as fluids are dispensed into wells 41 of microtiter plates during process cycles.

In one embodiment of the present invention, rotor assembly 46 includes a rotor 47 and a plate holder 101 (FIG. 2). Preferably rotor 47 is formed of a composite material, for example carbon fiber. Carbon fiber rotor 47 in accordance with the present invention is advantageous in that it is light weight, easy to balance and requires little maintenance. Such a carbon fiber rotor will not warp and thus will minimize the need for periodic balancing thereof. One should appreciate that the rotor can be made of other suitable materials such as metal and plastic.

Plate holder 101 (FIG. 2) is configured to dynamically alter the relative angle of microtiter plate 42 with respect to rotor 47. In particular, with reference to FIGS. 8(a) and 8(b), plate holder 101 is pivotally mounted on rotor assembly 46 by a pivotal support 102 located at an outer end 103 of the plate holder remote to the centrifugal axis of rotor assembly 46. Microtiter plate 42 is selectively engaged with plate holder 101 by a spring-biased latch mechanism 104.

A biasing mechanism 105 supports an inner end 106 of the plate holder with respect to rotor 47 intermediate pivotal support 102 and the centrifugal axis of the rotor assembly. Biasing member 105 includes a biasing spring 107 and an adjustable stop member 108. Biasing spring 107 biases plate holder 101 and microtiter plate 42 in a horizontal position against rotor 47 while the rotor assembly is stationary or moving slowly. Accordingly, microtiter plate 42 is in a horizontal position when reagent dispenser 52 is addressing the array of wells 41 on microtiter plate 42. Stop member 108 is adjustable such that the predetermined desired angle of tilt can be adjusted as necessary. In the embodiment shown in FIG. 8(b), inner end 106 serves as a hard stop against rotor 47. One should appreciate that an adjustable hard stop can be provided in order to provide means for finely adjusting the horizontal position of plate holder 101. Similarly, biasing mechanism 105 biases plate holder 101 against rotor assembly 46 into the horizontal position as rotor 47 decelerates.

When rotor assembly 46 is activated and begins to rotate, microtiter plates 42 increasingly tilt against the biasing force of spring 107 as centrifugal forces increase until plate holder 101 and microtiter plate 42 reach a desired predetermined angle. To accomplish this, the effect of increasing centrifugal force is utilized to move plate holder 101 and microtiter plate 42 to the desired angle. Specifically, a counter weight 109 is provided on outer end 103 at a location below pivotal support 102. As centrifugal forces on counter weight 109 increase and overcome the biasing force of spring 107, plate holder 101 and microtiter plate 42 tend to rotate about pivotal support 102 as shown in FIG. 8(b). In particular, as rotor 47 accelerates during centrifugation the centrifugal forces acting upon the combined centers of gravity of plate holder 101 and microtiter plate 40 overcome the force of gravity and the force of in the biasing mechanism 105.

One should appreciate that other suitable biasing mechanisms may be used for biasing plate holder 101 to horizontal position. For example, coil springs, torsion springs, leaf springs, and even gravity may be used for biasing plate holder 101 against rotor 47. An alternative biasing mechanism 111 is shown in FIG. 9 and is located on a central portion of rotor 47 adjacent the centrifugal axis. Biasing mechanism includes a biasing arm 112 connected to plate holder 101 by tension cable 113. Biasing arm 112 is biased toward a neutral position by torsion spring 114. As centrifugal forces increase, plate holder 101 begins to tilt and pulls on cable 113 and against the torsion force of torsion spring 112 thus moving arm 112 toward an adjustable stop bracket 115. Stop bracket 115 is easily adjusted by loosening a locking screw 116 and rotating stop bracket to a desired position which in turn adjusts the predetermined desired angle of plate holder 101 and microtiter plate 42.

Advantageously, the biasing mechanism of present invention provides a simple means which allows the delivery of liquid to microtiter plates within the rotor to take place with the microtiter plate in a horizontal position. This feature becomes increasingly important as well densities increase; that is, as the number of wells on a microtiter plate increase. This feature also become increasingly important as the diameter of the wells decrease and when liquid delivery takes place while either the microtiter plate or the reagent dispenser head is in motion. Since the plate is horizontal and thus normal to the array of nozzles during liquid delivery maximum target area of the wells is presented to the dispenser array. Advantageously, the biasing mechanism of the present invention also allows facile adjustment of the microtiter plate angle for dispensing cycles. The biasing mechanism allows easy access to the spring tension mechanism without removing the rotor from the apparatus.

In another embodiment of the present invention, the reaction vessel or well is formed of a porous polymeric material. It is commonly known that filtration may be used to separate liquids from a wetted substrate. Commonly, filtration is typically accomplished by centrifugation of the liquid through a discrete filter mesh or frit which is located at the bottom of a well or column in which oligonucleotide synthesis takes place. In one embodiment shown in FIG. 10(a), microtiter plate 121 and the array of wells 122 therein are formed of a porous polymeric material. Examples of suitable materials are TEFLON®, polyethylene, polypropylene and KYNAR®. Such porous polymeric materials are typically available in sheets, rods, tubes, and molded shapes. Such materials can be machined while maintaining its porous quality as long as the surface temperature of the material during machining does not reach the melting point of the material. One should appreciate that the shape of wells 122 may vary depending on the particular application and/or desired fluid dynamics. For example, the depth and diameter of the porous well may be U-shaped, V-shaped, or flat bottomed. Furthermore, the side wall of the well may be cylindrical, conically shaped, flat, tapered inwardly or outwardly, or have any other desired geometry. One should also appreciate that the shape of the microtiter plate itself may also vary. For example, instead of having a planar rectangular shape, the plate may include a planar surface having an arcuate shape, a triangular shape, or any other geometric shape as viewed from above depending upon the design of the rotor assembly.

Porosity of the material typically depends on the specific material and can be as low as 7 μm. Any such material can be used as long as the porosity is less than the maximum physical dimension of a substrate. For example, any material can be used for organic synthesis of oligomers as long as the porosity is less than the dimension of solid-phase particles such as a microbeads used in the synthesis. Alternatively, in the event that a discrete solid-phase particle is not used and the microtiter plate itself is used as the substrate, any porous polymeric material can be used as long as the porosity supports the liquid under the normal force of gravity but does not support the liquid under the higher forces of centrifugation.

One should appreciate that oligonucleotides can be synthesized not only in a microtiter plate having an array of wells, but may be synthesized in a porous rotor 123 (FIG. 10(b)) having a circumferential array of integral porous wells 124, or in a porous individual well 125 (FIG. 10(c)). The porous wells of the present invention beneficially reduces the complexity of filtration-based oligonucleotide synthesizers and provide an inherently simple tool for high-throughput synthesis of oligonucleotide. Not only do porous wells reduce the number of components of the rotor assembly, they also simplify maintenance of the rotor assemblies. Furthermore, porous wells in accordance with the present invention reduce rotor inertia intricacies of centrifugal synthesizers and therefore reduce cycle time. The porous wells of the present invention also increase the efficiency of "spill-over" based central synthesizers by decreasing the drying time required between sequential substrate exposures. Porous polymeric wells can also be reused for multiple synthesis in which radiation, thermal, chemical or other purification techniques are used to cleanse the wells. For example, the wells can be chemically purified by using a muriatic acid and water solution.

The porous wells in accordance with the present invention are particularly suited for reducing the complexity of filtration-based oligonucleotide synthesizers. The porous wells provide a simple means of simultaneous filtering of numerous wells, which promotes simplicity, efficiency, and high-throughput. Porous wells can also be used for proficient chemical labeling and/or modifying of oligonucleotide.

Alternatively, filtration, as well as reagent delivery, can be accomplished through frits on top of the microtiter well using centrifugation. In one embodiment of the present invention, a mesh 126 (FIG. 11(a)) is used to retain microbeads 127 in the wells. Mesh 126 or frit material can be placed over well 41 during centrifugation. Alternatively, mesh 126 can be used as the base of each well, as noted above. In either case, the use of mesh 126 during centrifugation retains beads 127 in the well, and therefore obviates the need for tilting the wells and/or microtiter plate at a critical angle of centrifugation because mesh 126 is fine enough to retain the beads but is sufficiently porous to allow the passage of liquids therethrough in the same manner as the porous polymeric material discussed above. Mesh 126 advantageously allows spent reaction liquid or washing solvents to be removed efficiently and completely. Also, very small quantities of microbeads 127 can be used without risk of loss. This allows smaller well volumes and thus higher well density, that is more wells per unit area of plate. This allows higher throughput and the ability to simultaneously synthesize a greater number of different compounds. Placement of mesh 126 above beads 127 allows a further level of control during reagent deliver because the reagents can be dispensed in bulk to all the wells, then delivered synchronously by centrifugation of wells 41 and causing the reagents to pass through mesh 126 of all wells simultaneously.

In operation and with reference to FIGS. 11(a)-(d), wells 41 of a microtiter plate (not shown in FIGS. 11(a)-(d)) contain beads 127 and a retaining mesh 126. Mesh 126 is shown recessed in well 41, however, one should appreciate that mesh 126 can alternatively be placed on top of well 41 and/or be used as the base of well 41. Liquid is then delivered to well 41. Because mesh is sufficiently fine, the liquid does not penetrate mesh 127 and enter into well 41 under the force of normal gravity. The liquid does not penetrate mesh 127 and enter well 41 until centrifugation is begun. The direction of the centrifugal force, indicated by arrow CF causes the liquid the pass through mesh and enter well 41 at which time reaction begins within the well. Liquid is expelled by reversing the direction of the centrifugal force as indicated by arrow CF' shown in FIG. 11(d). This may be accomplished by simply reversing the orientation of the well with respect to the rotor.

In another embodiment of the present invention, mesh 126 is provided at the base of well 41, as shown in FIGS. 12(a)-(b). In this embodiment, because the mesh is sufficiently fine, the liquid does not penetrate mesh 128 and exit well 41 through aperture 129 under the force of normal gravity. The liquid does penetrate mesh 128 and exit well 41 through aperture 129 under the force of centrifugation as expelled liquid indicated by arrow EL in FIG. 12(b). Similar to the above embodiment, mesh 128 retains the beads while liquid is expelled from well 41 by centrifugation. The use of mesh 128 also removes the need for a critical angle of centrifugation.

In yet another embodiment of the present invention, a less fine mesh 131 which does not impede the flow of liquid therethrough but is sufficiently fine to prevent microbeads 127 from passing therethrough is provided at the bottom of well 41, as shown in FIG. 13. Because mesh 131 does not retain liquid within the well, a sealing means 132 in the form of a biased seal or plug is provided to close aperture 133. A spring 134 is provided which biases sealing means against aperture 133 and when the rotor assembly is moving slowly or at rest. As centrifugation begins, the centrifugal forces acting on the liquid and the mass of the sealing means 132 overcome the biasing force of spring 134 and cause the sealing means to move away from the well thereby opening aperture 133 and allowing liquid to exit well 41. This configuration also obviates the need for tilted microtiter plates and the need for a critical angle of centrifugation.

Turning now to the control mechanism, a variety of different control mechanisms are used in synthetic reactions accordance with present invention. The present invention is adaptable to controls requiring manual intervention for some, or even all, processing steps of oligonucleotide (or other polymer) synthesis. The apparatus of the present invention is also adaptable to semi-automatic or fully-automatic controllers. Automatic control mechanisms should be sufficiently general that a different final compound can be synthesized in each reaction vessel or well of each array of wells utilized by the apparatus, and that a different combinatorial synthesis protocol can be performed each well and/or sets of wells. Finally, the automatic controller should be able to manage a plurality of wells, arrays of wells, fluid dispensers, rotor assemblies, and other work stations and subassemblies such that all components of the apparatus are optimally engaged or performing tasks for the synthesis.

The automatic control mechanisms are supported by certain hardware and software elements. General hardware elements preferably include one or more general control computers, an optional number of specialized control processors, and electrical interfaces to all controlled components of the apparatus. In a manner known in the art, all the directly and indirectly controlled components of the apparatus can be provided with electrical interfaces having certain standardized electrical characteristics. Certain of these low-level hardware interfaces are directly linked from their standardized interfaces to interfaces of the general control computers. Optionally, for complex resources, such as complex work stations, an intermediate level of specialized control processors is interposed between the general control computers and the low-level electrical interfaces of such resources.

The general control computers can be sufficiently capable personal computers (PC's) provided with such specialized electrical interfaces. An exemplary personal computer includes an Intel PENTIUM® processor running at 133 MHz, a 1 gigabyte or greater hard drive, 16 megabytes or more of memory, and commercially available interface boards providing interfaces such as D/A or on/off output circuits or links to standard instrument control buses. Specialized CPU's on custom PC boards for valve control, for example, an INTEL® 8051 compatible microprocessor, or other commercial motion control systems, for example, a COMPUMOTOR® 6K2, can be for low level control in accordance with the present invention. A PC running LINUX® and a custom designed control application (high level control) can be used to communicate with and control the low level controllers via ethernet and serial (e.g., RS-232) lines in accordance with the present invention. One should appreciate that such hardware control elements can be directly accessed or indirectly accessed via suitable internet or intranet connection.

General software elements executed by the general control computers include operating system software, low-level moment-to-moment control and monitoring software, scheduling and monitoring software, and synthesis planning software. At the lowest software level is the operating system software of the general control computers, which in an exemplary embodiment, can be UNIX® or WINDOWS NT® (Microsoft Corporation). The low-level moment-to-moment control and monitoring software inputs scripts describing in detail actions to perform and outputs electrical control signals to the controlled processing resources through the interfaces attached to the general control computers. These signals cause work station actions to be performed. At the next software level is scheduling software, which inputs a description of the synthetic steps to be performed, the locations of stored building blocks and reagents, the location and type of available work stations, the location and type of available interchangeable tools, and so forth, and outputs the detailed command scripts controlling subassembly functions. These scripts are interpreted by the moment-to-moment control and monitoring software. At the highest software level is chemical synthesis planning software, which inputs a description of the synthetic protocols available in a particular embodiment of the apparatus and the desired compounds to be synthesized, and then outputs the synthetic steps necessary to synthesize the desired compounds in a form usable by the scheduling software.

Various feedback controllers can be utilized to optimize the efficiency of oligonucleotide synthesizers in accordance with the present invention. For example, a plate reader 138 (FIG. 1) is provided on support surface 49 for real time monitoring of the chemical reactions in the wells during synthesis. In one embodiment of the present invention, plate reader 138 is an RS-170 color camera and frame grabber. Wetness monitors 139 are provided within support enclosure 45 in order to monitor leakage of the various liquids within the enclosure and thereby minimize down-time for maintenance and repair necessitated by leakage. Actuation of collection may also be employed in order to collect waste in an efficient manner in order to minimize waste disposal costs and/or promote recycling. For example, a two-way valve 141 is fluidly connected to a drum 142 which surrounds rotor assembly 46 for collecting liquid that is expelled from wells 41 during centrifugation. Two-way valve 141 selectively couples drum 142 with either a solvent catch basin 144 or a spent reaction fluid catch basin 145. In this manner, the liquids used during different synthesis processes, namely the addition and separation process and the washing process, are readily separated from one another.

In another embodiment of the present invention, an apparatus 150 (FIG. 14) is particularly suitable for use by individual users. Typical DNA synthesizers used in laboratories are relatively large, have a low capacity (for example only 4 to 16 oligonucleotides are made per run), are not fully automated, and require considerable attention. As a result, it is more cost-effective and time-efficient from the small labs to outsource oligonucleotide synthesis and manufacture. In contrast apparatus 150 is a compact oligonucleotide synthesizer, also referred to as a personal synthesizer, which has a very small footprint, is fully automated, and requires little or no attention during a run. Apparatus 150 is more cost-effective than outsourcing at present costs and can provide a quicker turned-round of small-scale synthesis and is particularly suited for high throughput, multi-protocol combinatorial syntheses. Furthermore, apparatus 150 has a small footprint and thus maximizes lab-top space. Apparatus 150 is adapted for synthesizing oligomers in each of a plurality of reaction vessels which are disposed in circular arrays, such as the circumferential array of reaction vessels or wells 122 (FIG. 10(b)). Apparatus 150 generally includes a support enclosure 155, a rotor assembly 123 (FIG. 10(b)) for supporting one or more wells 122, and a liquid delivery head 157. Support enclosure 155 provides mechanical support for the rotor assembly and liquid delivery head 15. The support enclosure 155 illustrated in FIG. 14 is approximately the same size as a desk-top printer. One should appreciate that the dimensions the personal synthesizer may vary.

Rotor assembly 123 is rotatably supported by support enclosure 155 and rotates about a centrifugal axis 158 which extends substantially orthogonal to the rotor assembly as wells as the desk-top or support surface upon which apparatus 150 is placed. Liquid delivery head 157 is a multi-channel dispenser including one or more solenoid valves 161 circumferentially spaced about centrifugal axis 158 and disposed concentrically with respect to the rotor assembly 123. Liquid delivery head is capable of simultaneously delivering a plurality of different liquids to corresponding different sets of wells 122 of the rotor assembly. Although ten solenoid valves 161 are shown, one should appreciate that one, two, three, or more valves may be provided depending upon the particular number of channels desired. Solenoid valves 161 are circumferentially spaced about a diameter which is substantially equal or approximate to the diameter of the circumferentially disposed wells 122 of rotor assembly 123. Accordingly, the dispensing nozzles associated with solenoid valves 161 are suspended in a circular pattern above wells 122 in the rotor assembly. The centrifugal motor which drives the rotor is capable of high acceleration and deceleration rates, velocities up to 4000 RPM, and positioning resolution of +/−0.2 degrees. Accordingly, specific ones of wells 122 can easily be aligned with any one of the dispensing nozzles.

Rotor 123 (FIG. 10(b)) of apparatus 150 can be configured to be a single-use and disposable item. Similarly, solenoid valves can self-contained and disposable cartridges which contain reagents, activators, and/or solvents. This embodiment combines the concept of the centrifuge synthesizer with the concept of a self-contained disposable liquid cartridge. The disposable liquid cartridge concept is similar to that employed in the field of desktop inkjet printers. This combination it is possible to produce a personal oligonucleotide synthesizer, a small low-cost, easy-to-operate, and highly automated device that can easily be programmed to perform custom synthesis of oligonucleotides as well as other molecules. In the event that self-contained, disposable cartridges are used, an operator of apparatus 150 does not have to weight, mix, and/or otherwise prepare reagents for use with apparatus 150. Instead, the operator simply inserts one or more cartridges in delivery head 157 which then automatically delivers controlled quantities of reagents to defined locations under computer control. The particular delivery pattern or delivery sequence of particular reagents determines the actual composition of the oligonucleotide being synthesized, much like the spatter or delivery of droplets of ink determines the content of a page printed by an inkjet printer.

One significant difference between the present invention and an inkjet printers is that inkjet printers typically use a small set of inks, for example black, red, blue, and yellow. The personal oligonucleotide synthesizer of the present invention is configured to receive a number of different reagent cartridges, thus allowing the synthesis of various molecules. For example, personal synthesizer 150 is provided with a plurality of different cartridges for various DNA reagents, RNA reagents, peptide reagents, fluorescent dyes and/or other chemical materials.

The personal oligonucleotide synthesizer 150 has a small rotor capable of up to 96 synthesis procedures at one time because it includes 96 concentrically spaced wells. One should appreciate that lesser or greater capacities can be incorporated depending upon the number of wells provided. Reaction wells 122 of rotor 123 may be arranged in a single circle (not shown) or in concentric circles of wells 122, 122' (FIG. 10(b)) in order to increase the capacity of both the rotor and the personal synthesizer 150. On should also appreciate that the rotor can be configured to receive curved microtiter plates 163 as is shown in FIG. 15. The curved microtiter plates are selectively secured to the rotor assembly by suitable means such as a spring biased latch. In any event, solid-phase support is contained within the wells of the rotor in the form of microbeads, or other suitable solids, in a similar manner to that discussed above. Alternatively, a derivatized membrane may be used within the wells instead of and/or in addition to the microbeads.

As shown in FIG. 14, apparatus 150 includes an array of the nozzles that is arranged radially along the perimeter of the rotor assembly which significantly simplifies the process of addition and removing liquids from wells 122. In fact, delivery head 157 can deliver liquid to wells 122 while the rotor is still moving in a similar manner as discussed above. Discrete high-speed control of solenoid valves 161 are controlled dependant upon, pressure, time, volume, and the speed at which rotor assembly 123 is moving. Such a configuration allows the liquid delivery head to deliver liquid to all the wells located in the rotor assembly in approximately 8 to 10 seconds.

In the case the personal synthetizer is provided with a rotor having two or more concentric arrays of wells, a spiral translation mechanism 163 (FIG. 16) would be incorporated into liquid delivery head 157 in order to adjustably support the dispensing nozzles 164. Spiral translation mechanism 164 includes two circular structures, one static disc 165 and one dynamic disc 166. Static disc 165 contains slots 168 running from its center toward its periphery in a radial pattern. Slots 168 are wide enough to slidably accommodate dispensing nozzles 164 along a radial path. Dynamic disc 166 includes an identical number of curved slots 168 milled to approximately the same width also running from the central portion of dynamic disc 166 to the periphery thereof in a arcuate path. Static disc 165 and dynamic disc 166 are concentrically and rotatably mounted with respect to the other. Nozzles 164 are mounted substantially vertically within the slots at each point where the path of a straight slot 168 crosses the path of a curved slot 169. When static disc 165 and dynamic disc 166 are rotated relative to one another, nozzles 164 moved directly along the path of the straight slots 168. This configuration this allows precise synchronized control of the nozzle locations about the central axis. Dynamic disc 166 can be controlled by an actuator such as a stepper motor, air cylinder, rack and pinion structure, rotor-drive stepper motor, or any other suitable means.

Apparatus includes a locking actuator, for example an air cylinder plunger 171 schematically shown in FIG. 16(*a*), which is mounted on dynamic disc 166 over the center of rotor assembly 123. Actuator 171 would extend downwardly toward the top of rotor assembly 123. Actuator 171 includes a non-rotating shaft. The end of the shaft selectively engages the top of rotor assembly 123. Actuator 171 also contains a brake which is engaged with static disk 165 whenever actuator 171 is not actuated thereby holding the nozzle array in a set position. When relocation of the nozzle array is desired, rotor assembly 123 stops in alignment with actuator 171 because the particular position is remembered from the last operation. Actuator 171 is actuated and it engages rotor assembly 123 and disengages the brake. Rotor assembly 123 rotates to a position that is supplied from a lookup data table stored in control software. Actuator 171 disengages from rotor assembly 123 and reengages the brake. The system is now ready to access the next array of wells. This process control allows location of the concentric ring of nozzles about the center and supports dispensing to multiple concentric rings of wells within rotor assembly 123.

Apparatus 150 may also use a variety of different control mechanisms in accordance with present invention. The present invention is adaptable to controls requiring manual intervention for certain, or even all, processing steps of oligonucleotide synthesis. The apparatus of the present invention is also adaptable to semi-automatic or fully-automatic controllers which are run by personal computers. In one embodiment of the present invention, personal synthesizer 150 is controlled by a PC or with a hand held personal computing device which synchronize with a PC. In the case of the latter, an infrared port 174 (FIG. 14) is provided on support enclosure 155 thus allowing an operator to synchronize data and otherwise check the status of the personal synthesizer. Preferably, basic parameters will be displayed directly on the personal synthesizer or readily displayed on the personal computing device in order to minimize the need of a PC in the vicinity of the personal synthesizer and thereby free up critical lab-top workspace.

One disadvantage associated with conventional oligonucleotide synthesis is scaling the technology to increase numbers. An apparatus 180 (FIG. 17(*a*)) in accordance with a present invention allows a large number of oligonucleotides to be synthesized easily and cost effectively. Apparatus 180 includes a support mechanism 181 which rotatably supports a plurality of microtiter plates 42. Specifically, mechanism 181 is capable of holding microtiter plates 42 in either an upright or an inverted position. When plates 42 are an upright position, reagent dispensing head 182 addresses plates 42 and delivers individual reagents into the wells of plates 42. When plates 42 are in an inverted position, the plates can be washed with the appropriate reagents dispensed by wash head 183. This configuration creates an effective format delivering reagents and washing the plates, typically the most difficult and time-consuming step in the process. Mechanism 181 may include a conveyor belt 184, a chain drive system, an axes driven system 185 (FIG. 17(*b*)), or any other suitable drive system for translating and inverting the microtiter plates.

Advantageously, apparatus 180 provides a high-throughput chemical synthesis instrument which may be used for oligonucleotide synthesis. Because microtiter plates 42 are conveniently inverted for washing, the apparatus creates a physical dimension that is independent from the dimension used for base addition.

Microtiter plates 42 are derivatized to allow base addition therein. As this is accomplished by derivatizing commercially available plates with an amine or an —OH functionality.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed:

1. An apparatus for dispensing liquids into a reaction vessel, said apparatus comprising:
   a rotor mounted for rotation about a central axis, said rotor carrying an array of reaction vessels along a circular path;
   a liquid dispenser comprising a plurality of dispensing nozzles, said liquid dispenser positioned above said rotor and arranged for dispensing a liquid from each dispensing nozzle into a reaction vessel while said array of reaction vessels moves along said circular path, wherein said dispensing nozzles are configured such that movement of the dispensing nozzles is minimized or eliminated; and
   a controller for synchronizing movement of said rotor with the dispensing of the liquid such that said liquid dispenser dispenses the liquid into said array while said rotor is rotating.

2. The apparatus of claim 1 wherein said apparatus is configured for chemical synthesis and said liquid dispenser is fluidly coupled with one or more reagent sources.

3. The apparatus of claim 2 wherein said apparatus is configured for synthesis of oligomers.

4. The apparatus of claim 1 wherein each of said dispensing nozzles comprises a dispensing valve controlling liquid delivery thereto, wherein said controller is configured to simultaneously synchronize movement of said rotor and control of said dispensing valve.

5. The apparatus of claim 4 wherein at least one dispensing valve comprises an electric solenoid valve.

6. The apparatus of claim 1 wherein said controller is configured to actuate said nozzles and dispense fluid while said rotor is moving along said circular path.

7. The apparatus of claim 1 wherein said plurality of dispensing nozzles are linearly arranged in a pattern corresponding to a radial column of said array of reaction vessels.

8. The apparatus of claim 1 wherein said liquid dispenser is a multi-channel dispenser.

9. A method for dispensing liquids into a reaction vessel, said method comprising:

providing a rotor and a liquid dispenser, said rotor being mounted for rotation about a central axis and carrying an array of reaction vessels along a circular path, said liquid dispenser comprising a plurality of dispensing nozzles and being positioned above said rotor;

dispensing a liquid from each dispensing nozzle into a reaction vessel while said array of reaction vessels moves along said circular path, wherein said dispensing nozzles are configured such that movement of the dispensing nozzles is minimized or eliminated; and synchronizing movement of said rotor with the dispensing of the liquid such that said liquid dispenser dispenses the liquid into said array while said rotor is rotating.

10. The method of claim 9 further comprising performing chemical synthesis in at least one of said reaction vessels.

11. The method of claim 10 wherein said performing chemical synthesis comprises synthesis of oligomers.

12. The method of claim 9 wherein each of said nozzles comprises a dispensing valve controlling liquid delivery thereto, wherein said synchronizing step further comprises controlling said dispensing valve.

13. The method of claim 12 wherein at least one dispensing valve comprises an electric solenoid valve.

14. The method of claim 9 further comprising simultaneously delivering different liquids to respective ones of said reaction vessels.

15. The method of claim 14 further comprising actuating said nozzles and dispensing fluid while said rotor is moving along said circular path.

* * * * *

UNITED STATES PATENT AND TRADEMARK OFFICE
Certificate

Patent No. 7,390,459 B2                                                          Patented: June 24, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michal Lebl, San Diego, CA (US); David L. Heiner, San Diego, CA (US); Mark S. Chee, Encintas, CA (US); Vit Pokorny, Praha (CZ); and Mark J. Nibbe, Oceanside, CA (US).

Signed and Sealed this Sixteenth Day of February 2010.

*JILL A. WARDEN*
*Supervisory Patent Examiner*
*Art Unit 1797*